United States Patent
Hoyes et al.

(10) Patent No.: US 9,728,391 B2
(45) Date of Patent: *Aug. 8, 2017

(54) ORTHOGONAL ACCELERATION COAXIAL CYLINDER TIME OF FLIGHT MASS ANALYSER

(71) Applicant: Micromass UK Limited, Wilmslow (GB)

(72) Inventors: John Brian Hoyes, Stockport (GB); David J. Langridge, Macclesfield (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,683

(22) PCT Filed: May 16, 2013

(86) PCT No.: PCT/GB2013/051269
§ 371 (c)(1),
(2) Date: Nov. 17, 2014

(87) PCT Pub. No.: WO2013/171499
PCT Pub. Date: Nov. 21, 2013

(65) Prior Publication Data
US 2015/0136970 A1 May 21, 2015

Related U.S. Application Data

(60) Provisional application No. 61/650,008, filed on May 22, 2012.

(30) Foreign Application Priority Data

May 18, 2012 (GB) .................................. 1208847.2
May 21, 2012 (EP) .................................. 12168612
(Continued)

(51) Int. Cl.
*H01J 49/40* (2006.01)
*H01J 49/00* (2006.01)

(52) U.S. Cl.
CPC .......... *H01J 49/401* (2013.01); *H01J 49/405* (2013.01); *H01J 49/406* (2013.01); *H01J 49/408* (2013.01); *H01J 49/0031* (2013.01)

(58) Field of Classification Search
CPC ........ H01J 49/401; H01J 49/405; H01J 49/46; H01J 49/408
See application file for complete search history.

(56) References Cited

U.S. PATENT DOCUMENTS 8,642,955 B2 * 2/2014 Austin ................ H01J 49/0013
250/281
8,853,623 B2 10/2014 Verenchikov
(Continued)

FOREIGN PATENT DOCUMENTS

GB 2470599 12/2010
GB 2482785 2/2012
(Continued)

OTHER PUBLICATIONS

Watkins, The Helitron Oscillator, Proceedings of the IRE, 1958.*
Bakker, "The Spiratron", Adv. In Mass Spectrom., 1971, v.5, pp. 278-280.*

*Primary Examiner* — Wyatt Stoffa
*Assistant Examiner* — James Choi
(74) *Attorney, Agent, or Firm* — Diederiks & Whitelaw, PLC

(57) ABSTRACT

A Time of Flight mass analyzer is disclosed comprising an annular ion guide having a longitudinal axis and comprising a first annular ion guide section and a second annular ion guide section. Ions are introduced into the first annular ion guide section so that the ions form substantially stable circular orbits within the first annular ion guide section about the longitudinal axis. An ion detector is disposed within the annular ion guide. Ions are orthogonally accelerated in a first axial direction from the first annular ion
(Continued)

guide section into the second annular ion guide section. An axial DC potential is maintained along at least a portion of the second annular ion guide section so that the ions are reflected in a second axial direction which is substantially opposed to the first axial direction. The ions undergo multiple axial passes through the second annular ion guide section before being detected by the ion detector.

35 Claims, 32 Drawing Sheets

(30) Foreign Application Priority Data

| Sep. 14, 2012 | (GB) | 1216486.9 |
| Sep. 14, 2012 | (GB) | 1216488.5 |
| Sep. 14, 2012 | (GB) | 1216489.3 |

(56) References Cited

U.S. PATENT DOCUMENTS

| 9,343,285 B2* | 5/2016 | Green | H01J 49/065 |
| 9,466,473 B2* | 10/2016 | Giles | G01N 27/622 |
| 2004/0119012 A1* | 6/2004 | Vestal | H01J 49/025 |
| | | | 250/287 |
| 2005/0087684 A1* | 4/2005 | Farnsworth | G01N 30/72 |
| | | | 250/287 |
| 2005/0242279 A1* | 11/2005 | Verentchikov | H01J 49/40 |
| | | | 250/287 |
| 2005/0285030 A1 | 12/2005 | Farnsworth | |
| 2009/0078866 A1* | 3/2009 | Li et al. | 250/297 |
| 2012/0138785 A1* | 6/2012 | Makarov et al. | 250/282 |
| 2012/0153140 A1* | 6/2012 | Makarov | 250/282 |
| 2013/0068942 A1* | 3/2013 | Verenchikov | H01J 49/4245 |
| | | | 250/282 |
| 2014/0217275 A1 | 8/2014 | Ding et al. | |
| 2014/0246575 A1* | 9/2014 | Langridge | H01J 49/025 |
| | | | 250/282 |
| 2014/0284471 A1* | 9/2014 | Brown | H01J 49/06 |
| | | | 250/282 |
| 2014/0291503 A1* | 10/2014 | Shchepunov | H01J 49/408 |
| | | | 250/282 |
| 2015/0048246 A1* | 2/2015 | Green | H01J 49/065 |
| | | | 250/283 |
| 2015/0136970 A1* | 5/2015 | Hoyes | H01J 49/401 |
| | | | 250/282 |

FOREIGN PATENT DOCUMENTS

| GB | 2486584 | 6/2012 |
| WO | 2005/040785 | 5/2005 |

* cited by examiner

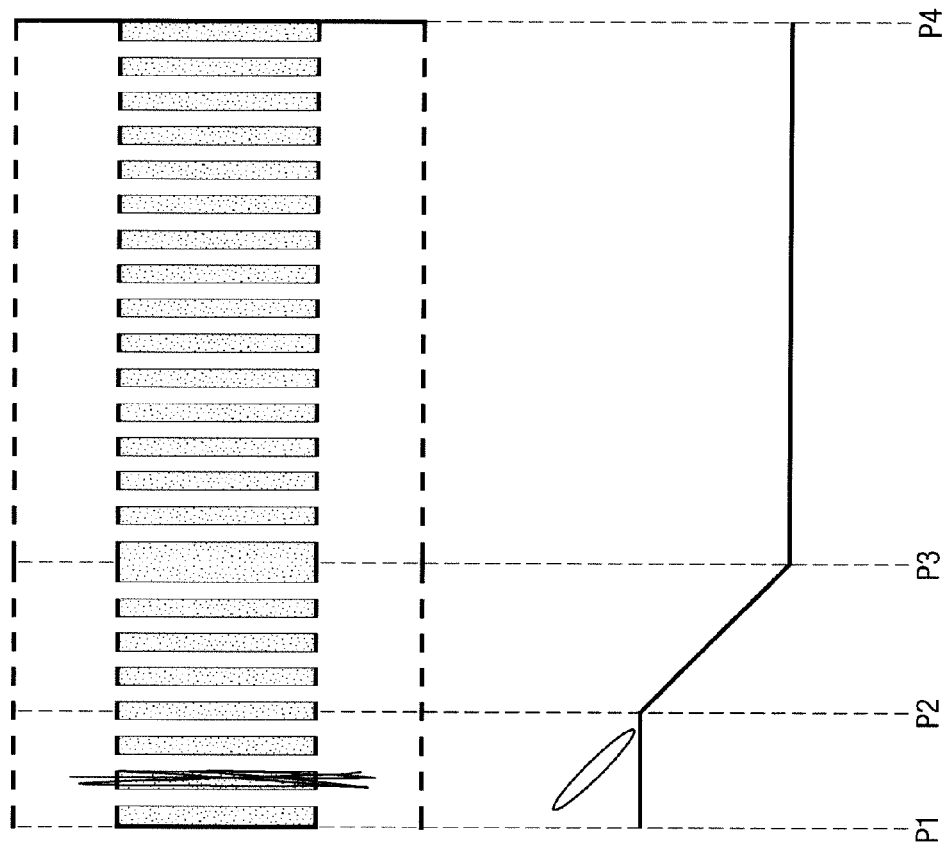
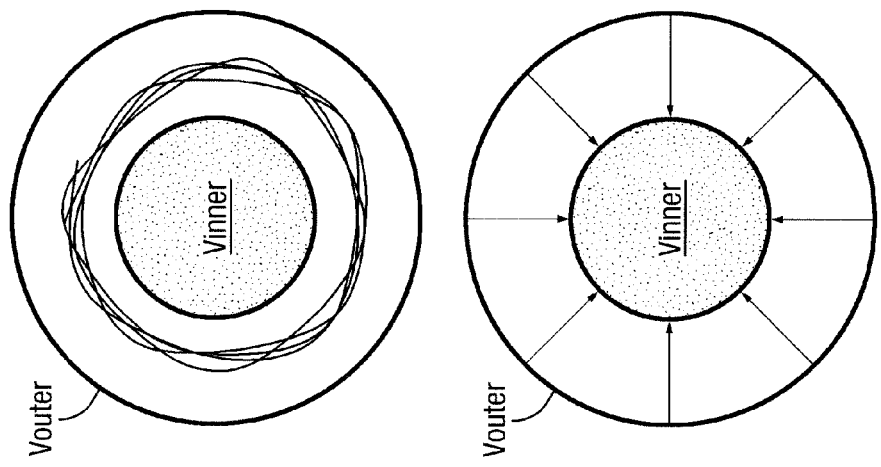
Fig. 6a

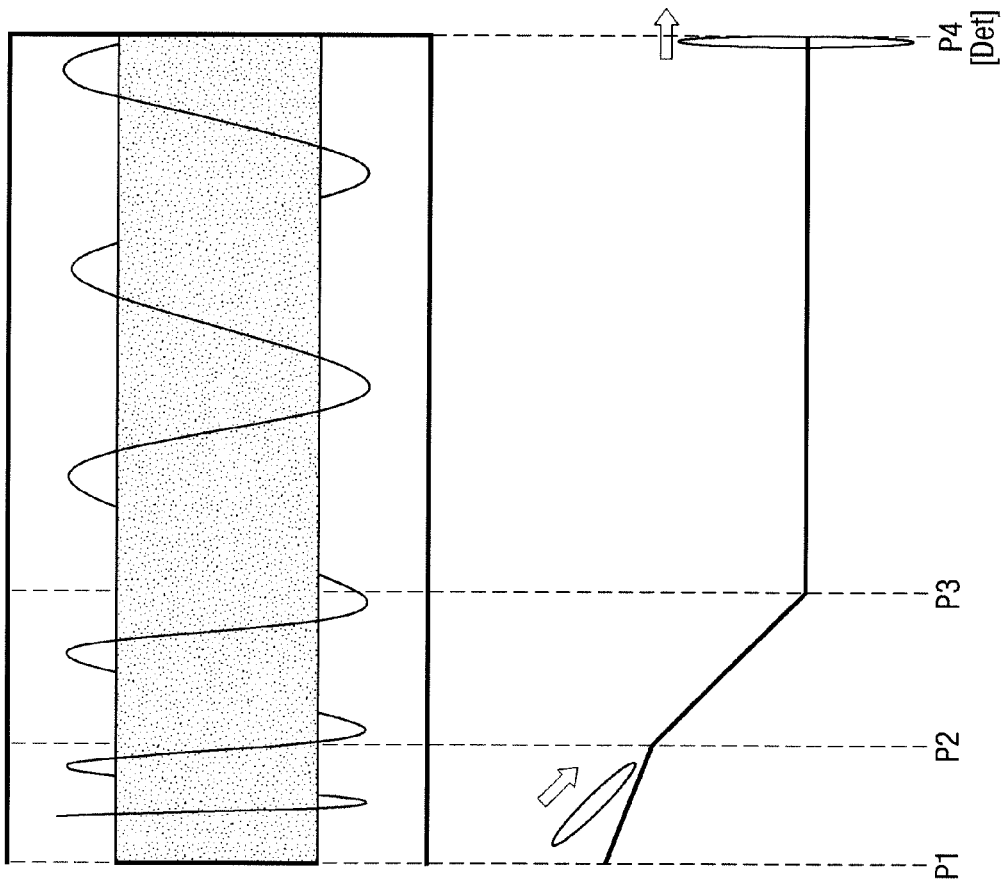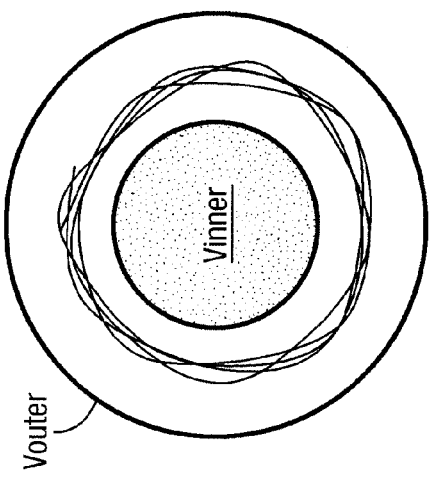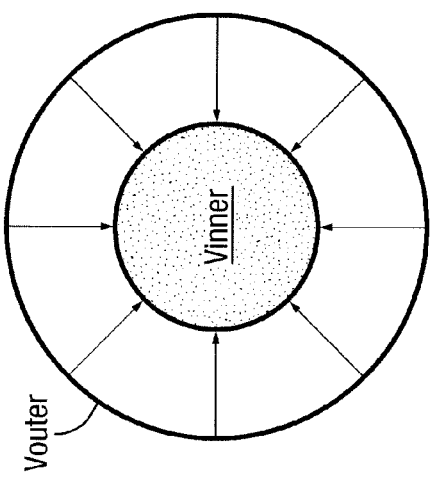
Fig. 6b

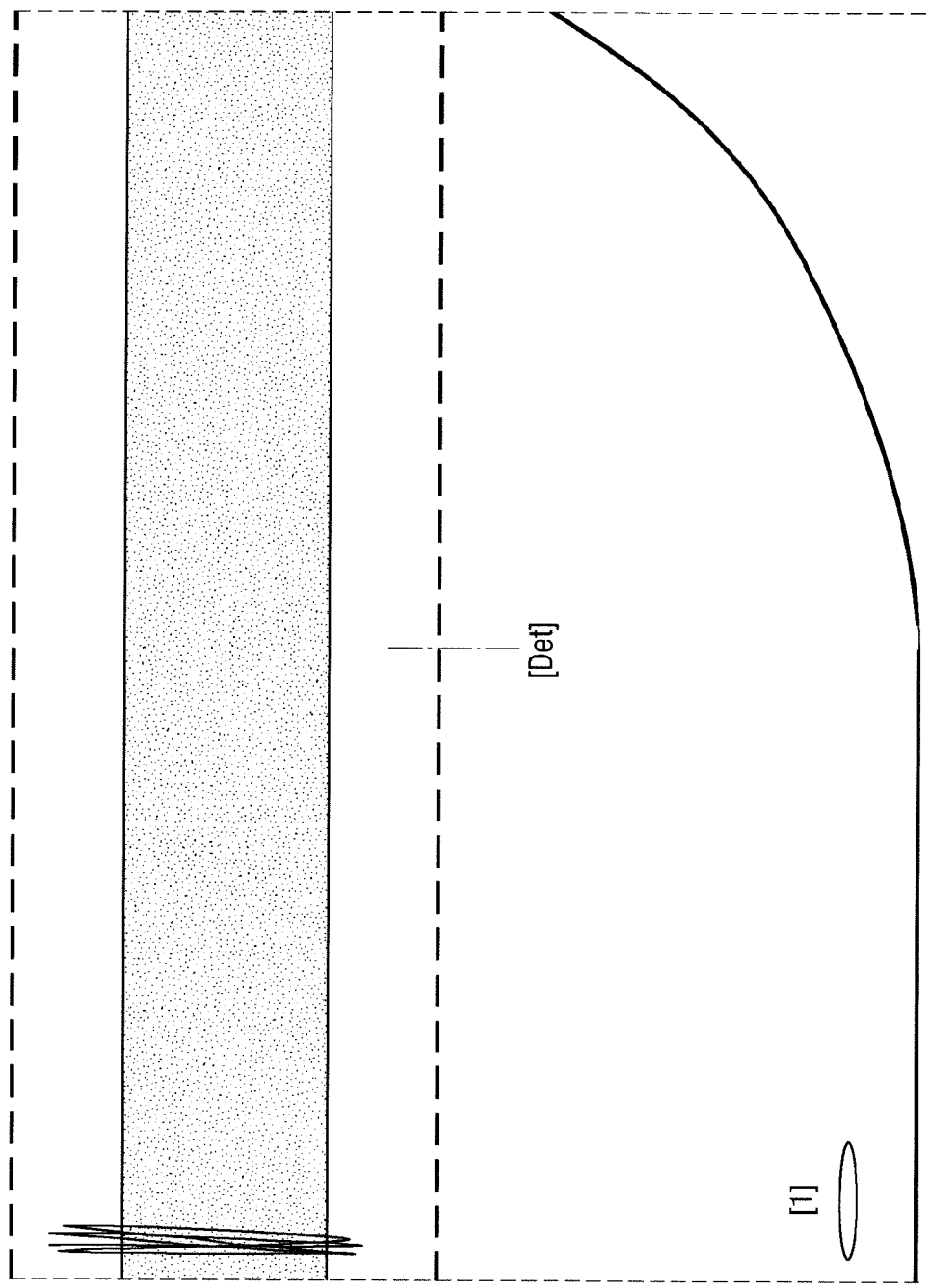

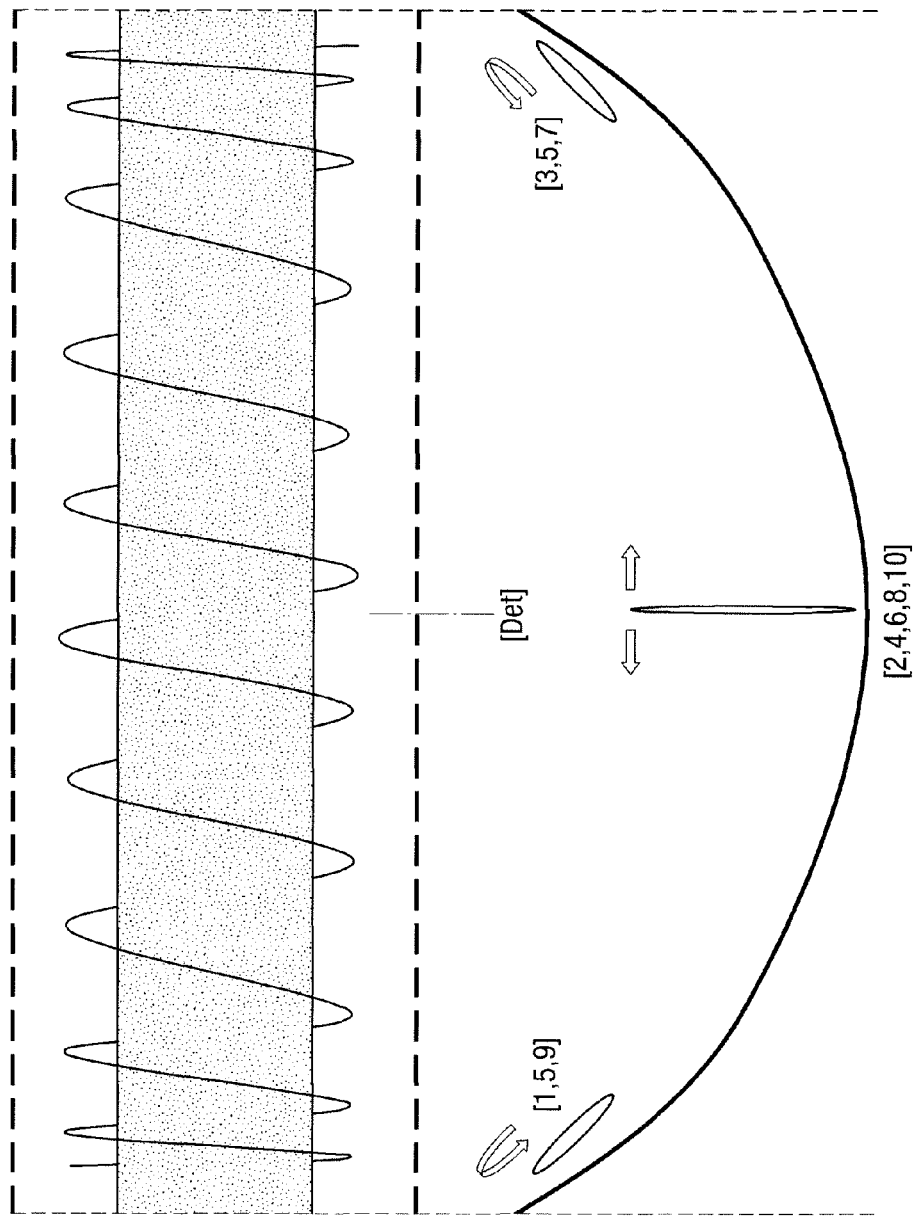

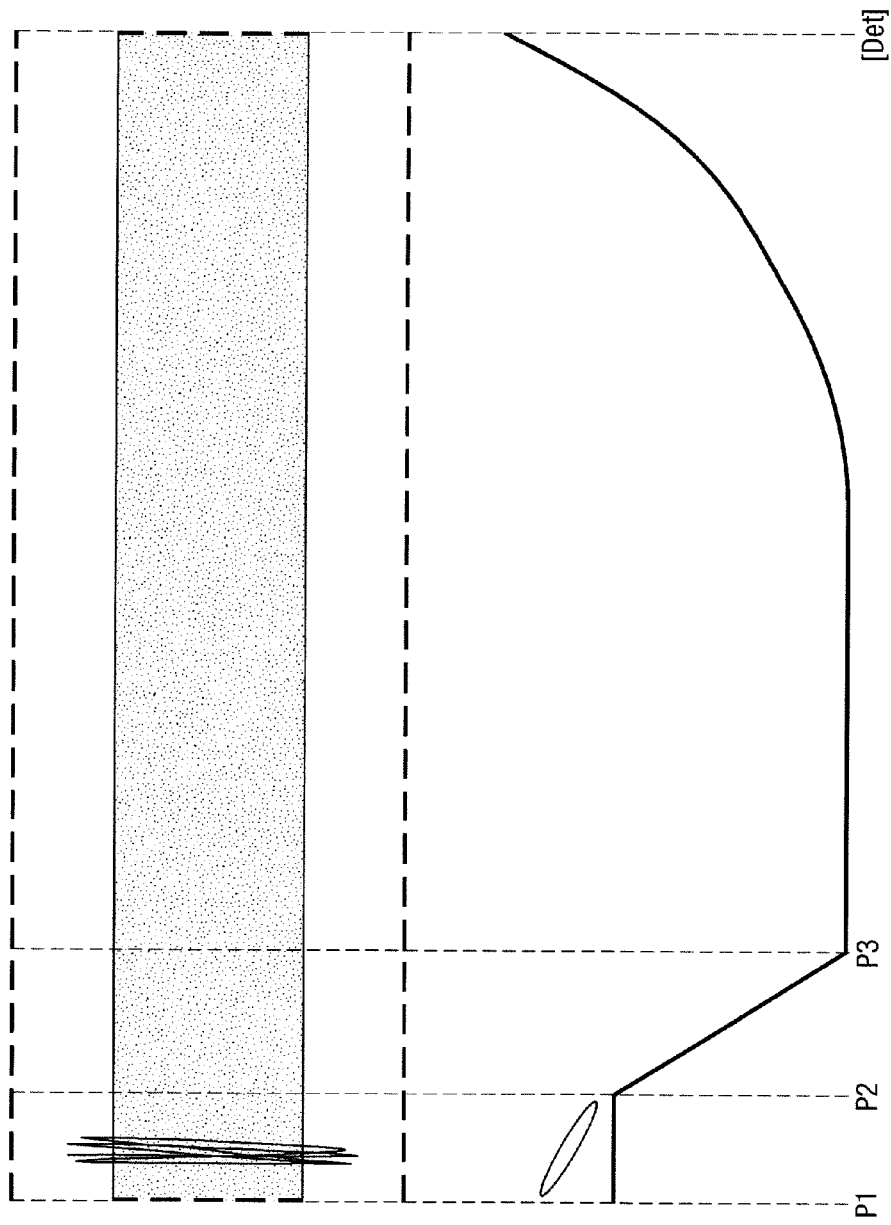

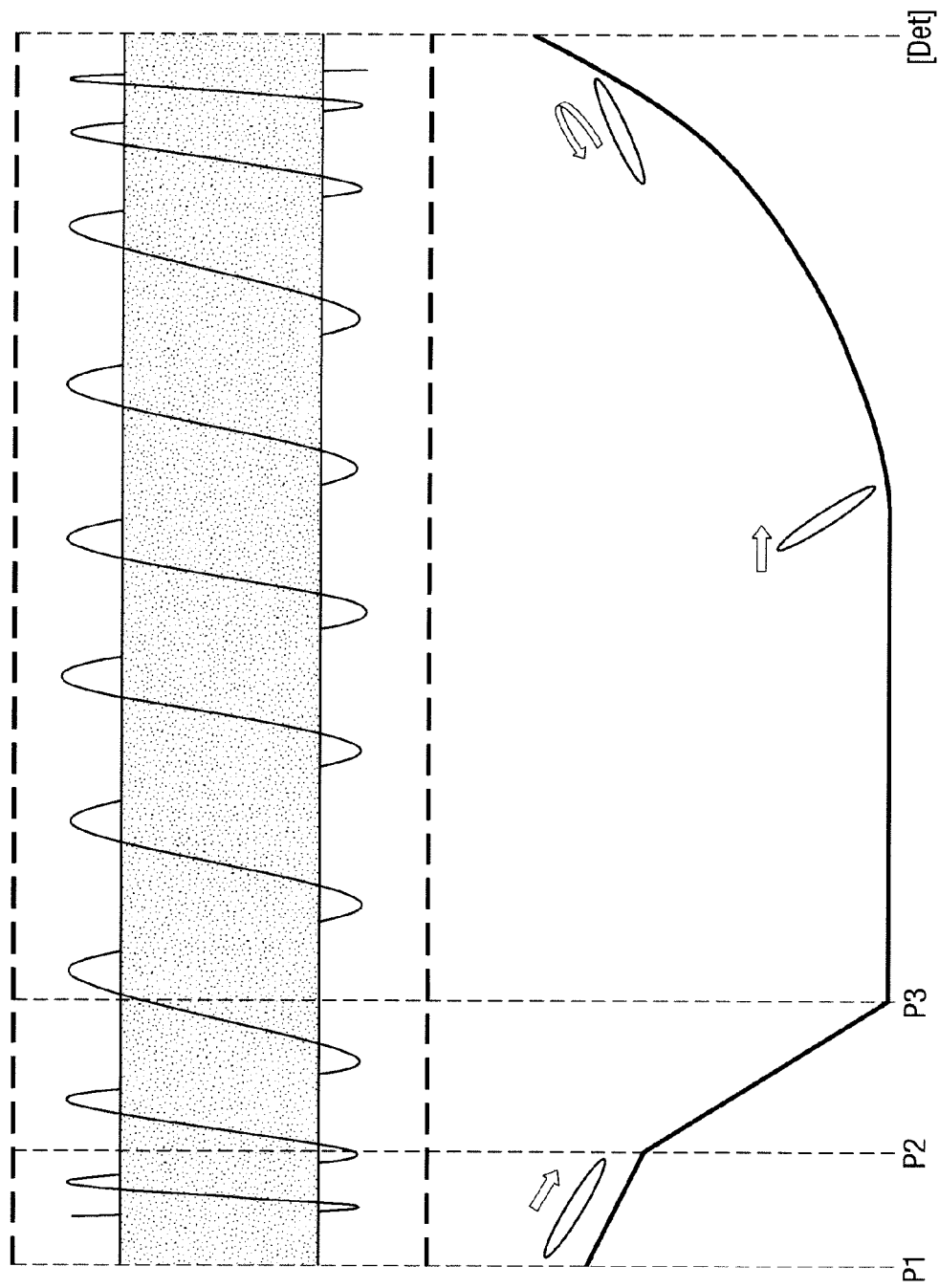

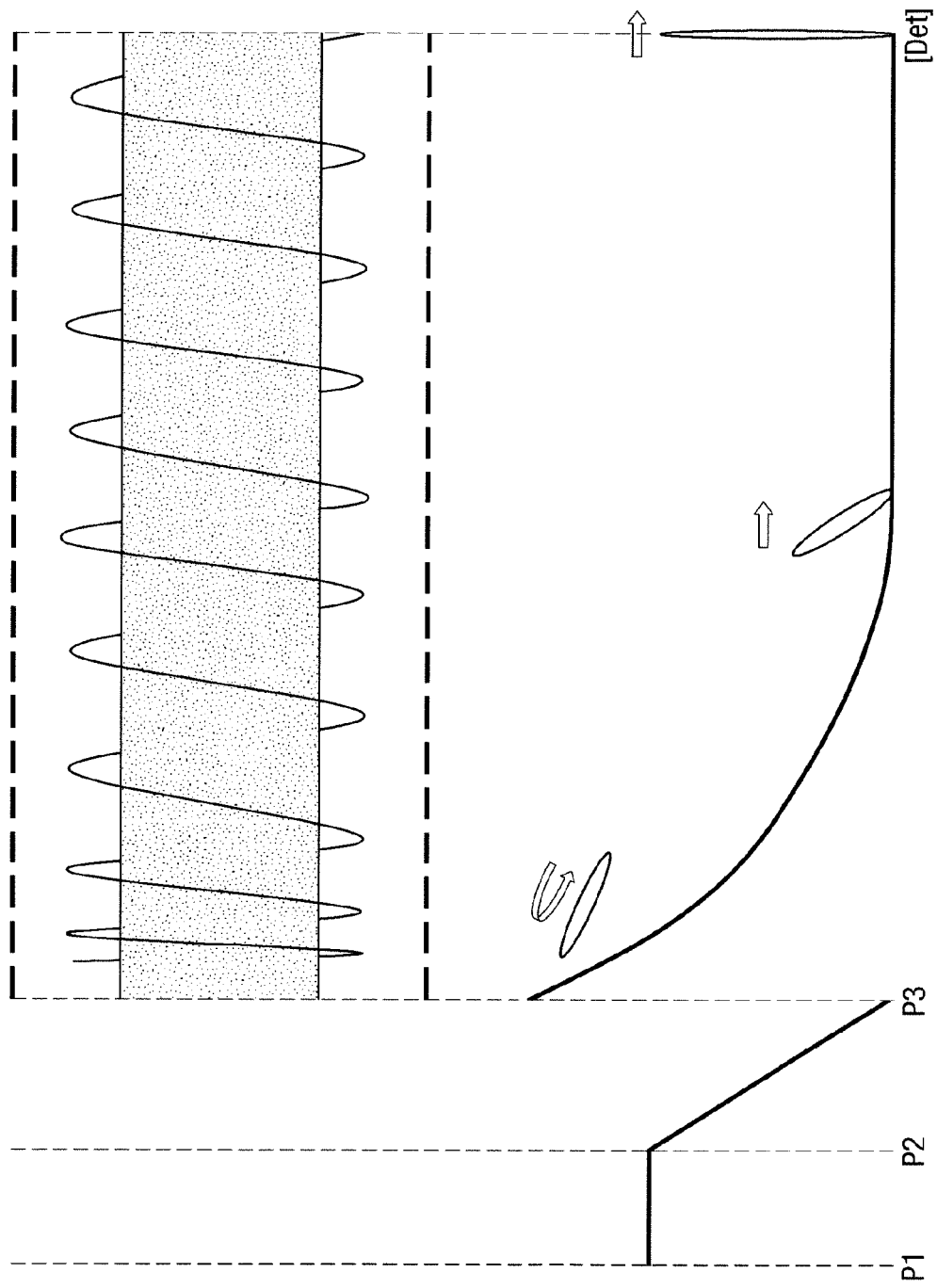

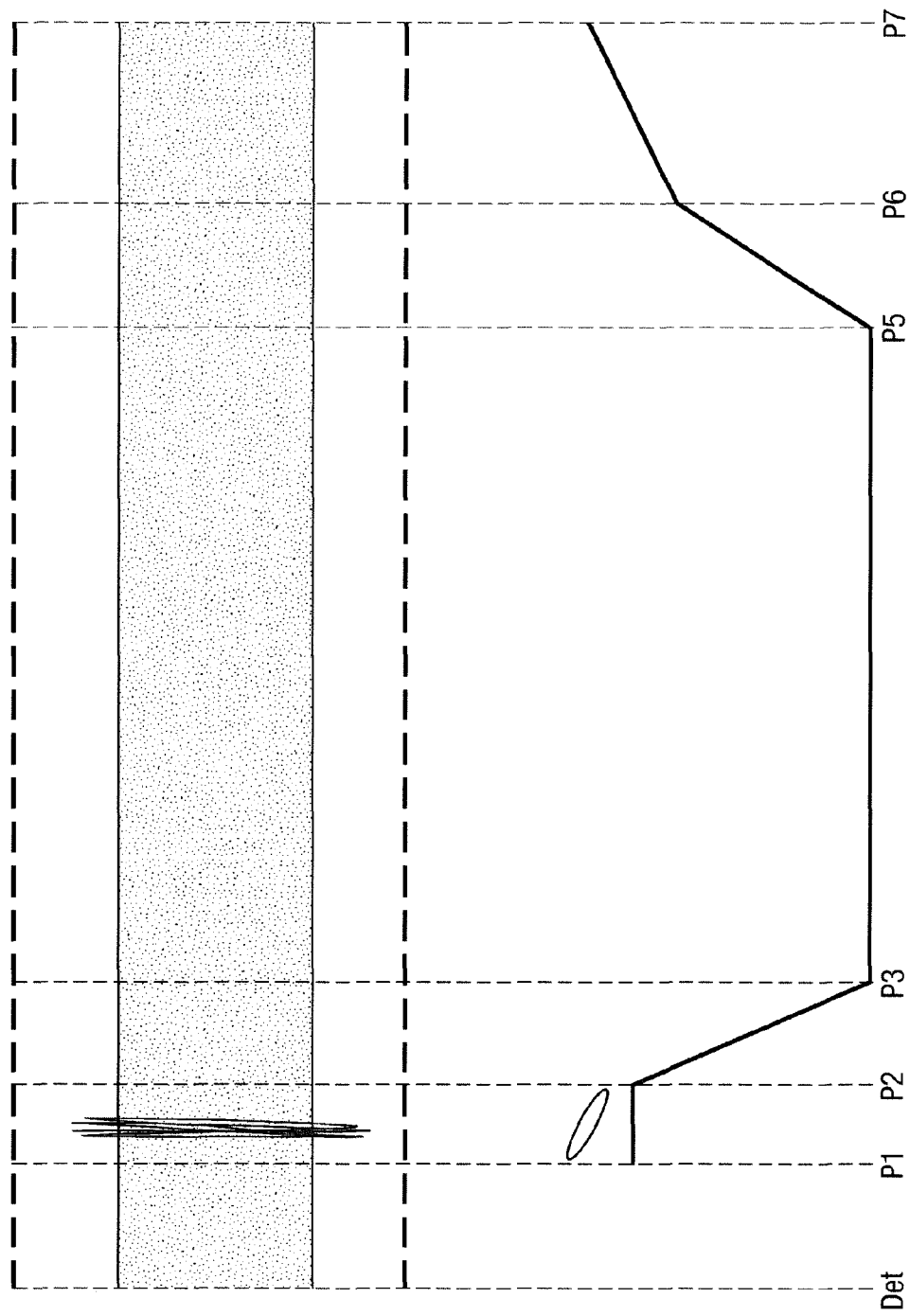

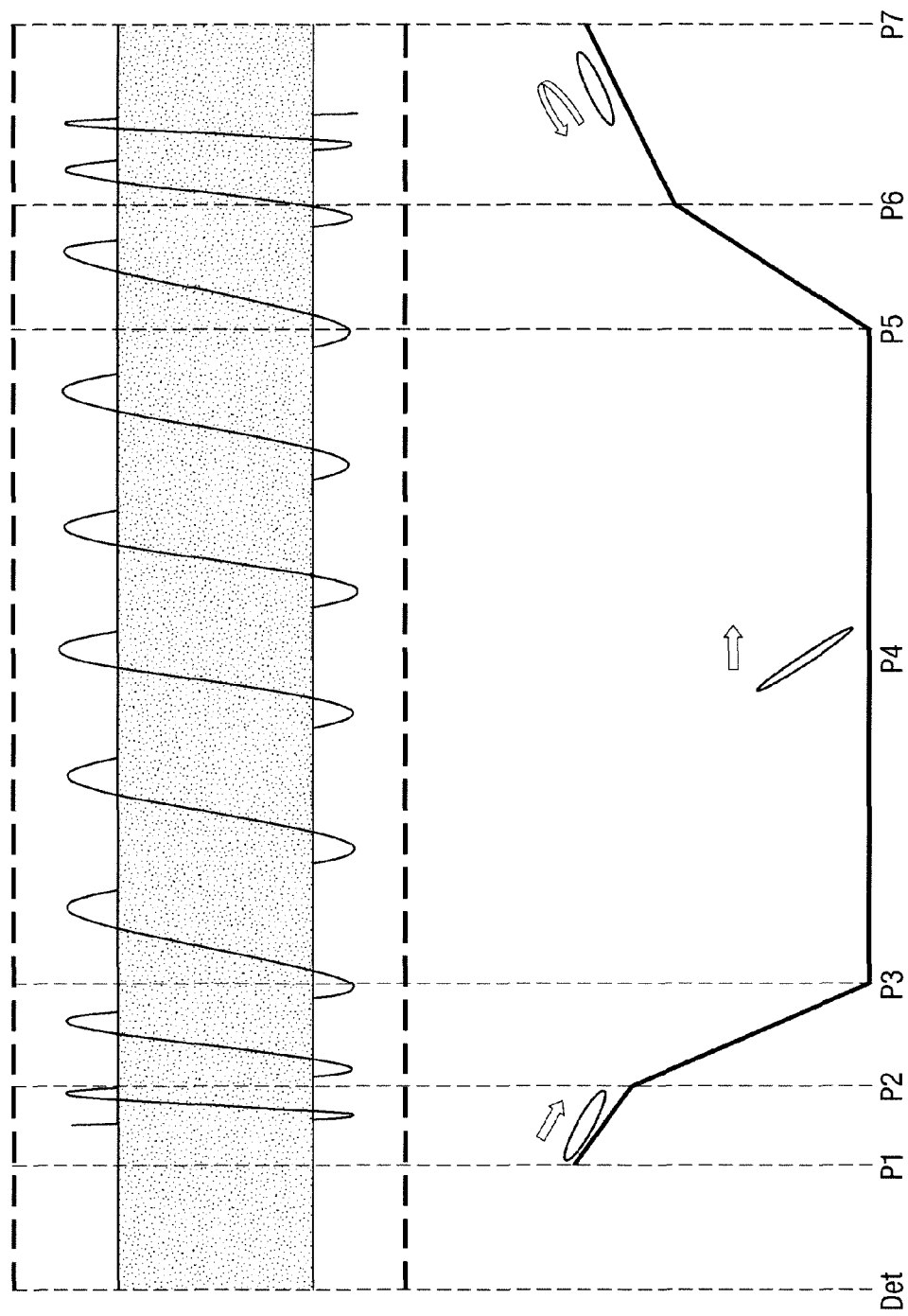

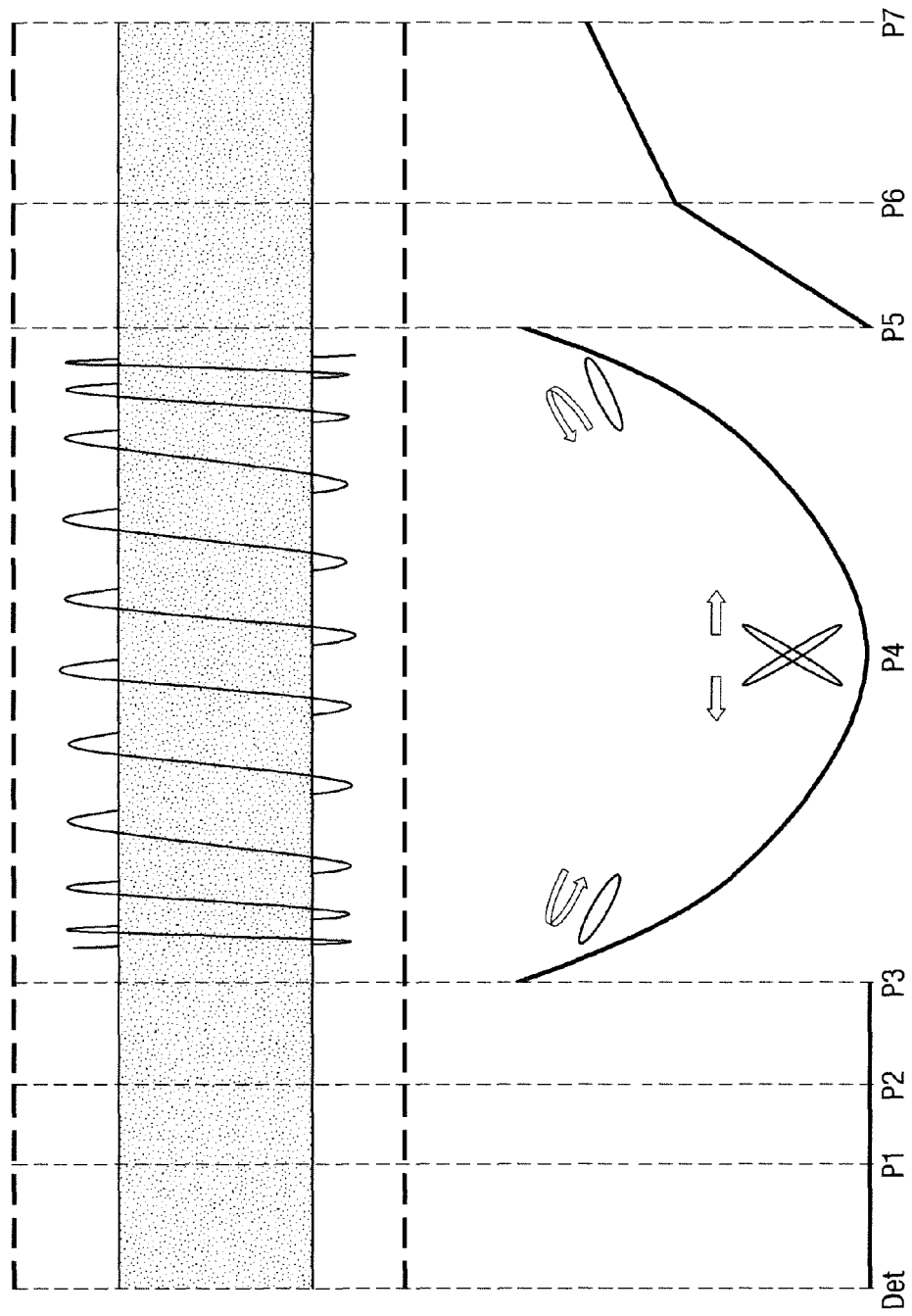

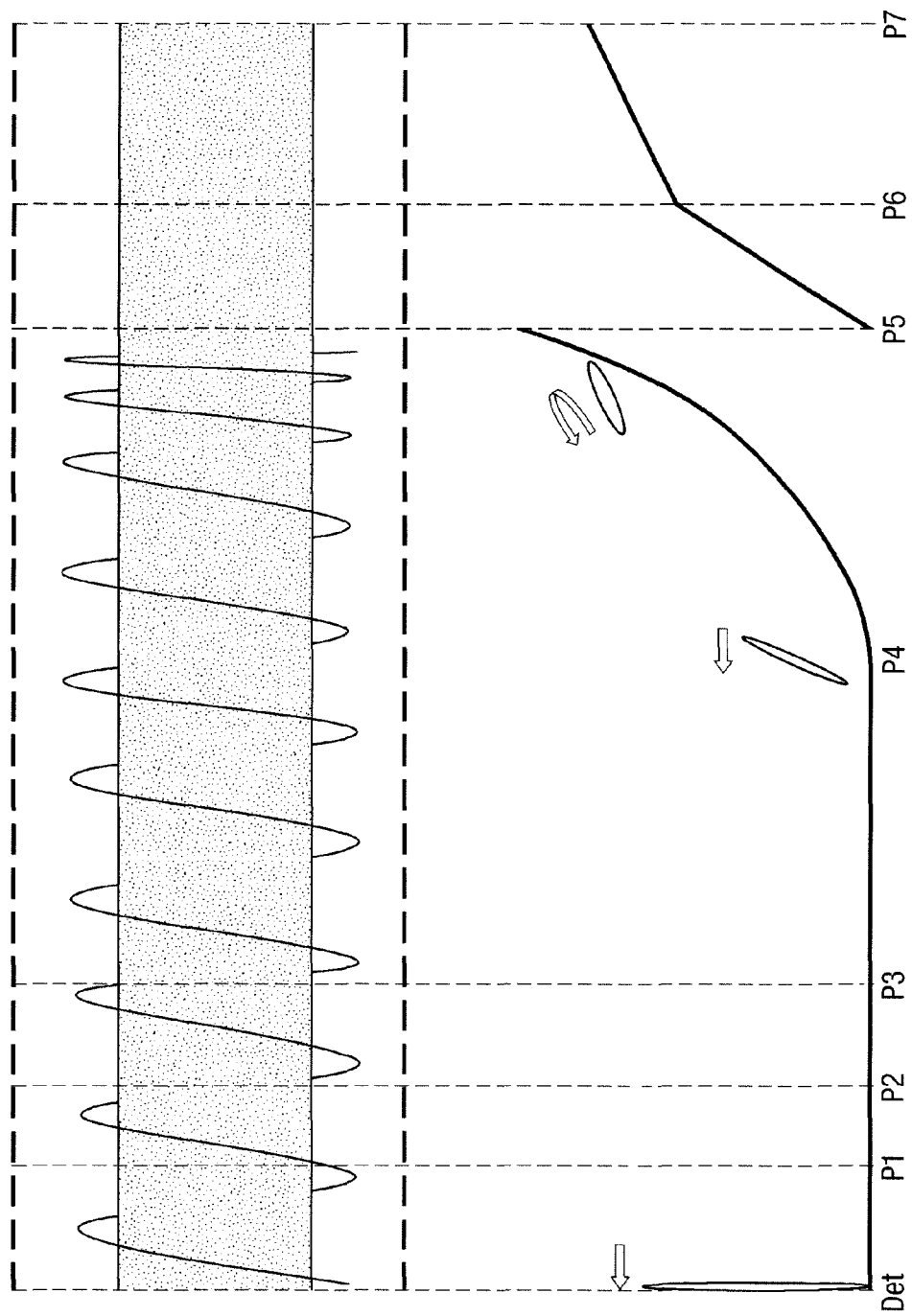

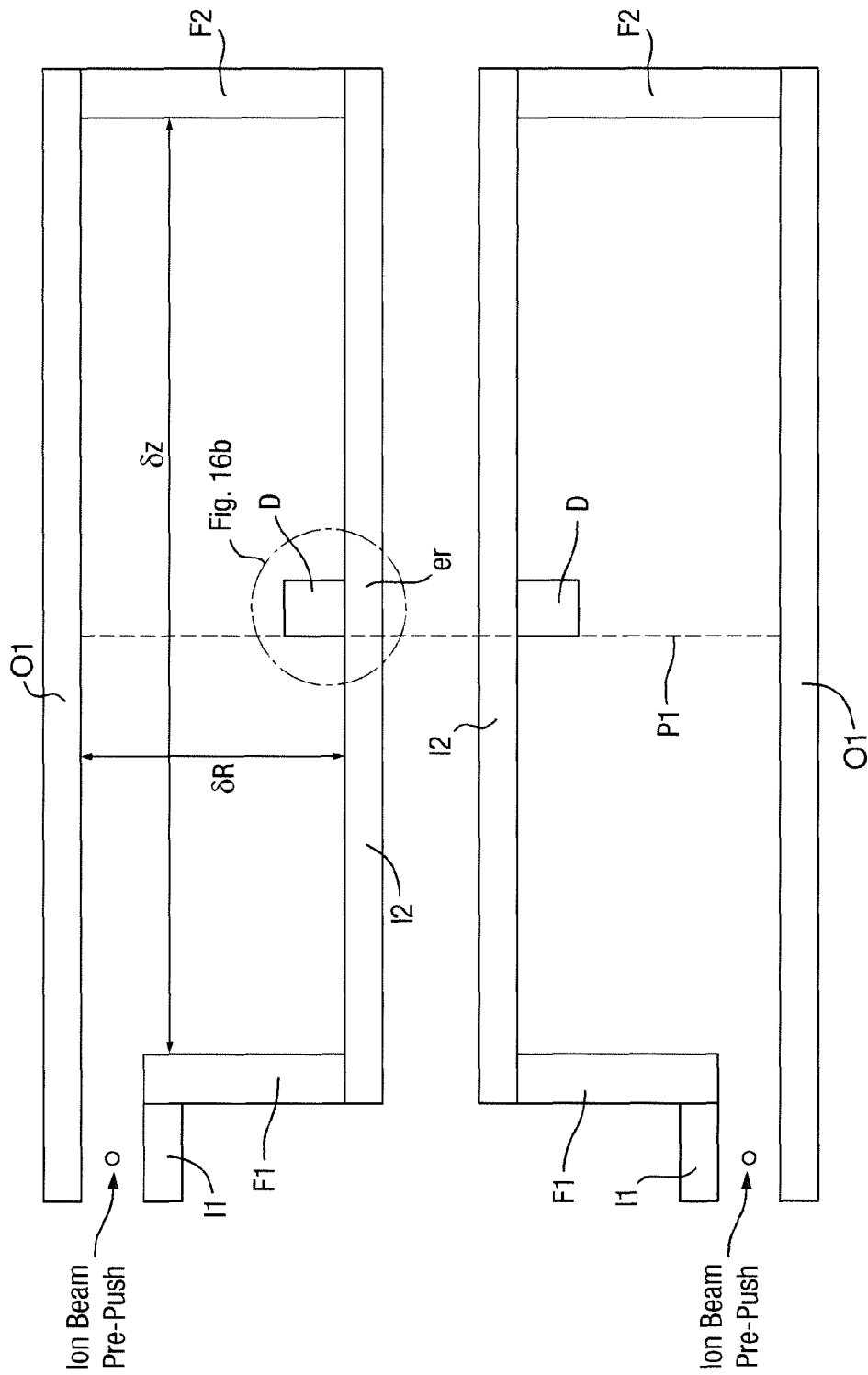

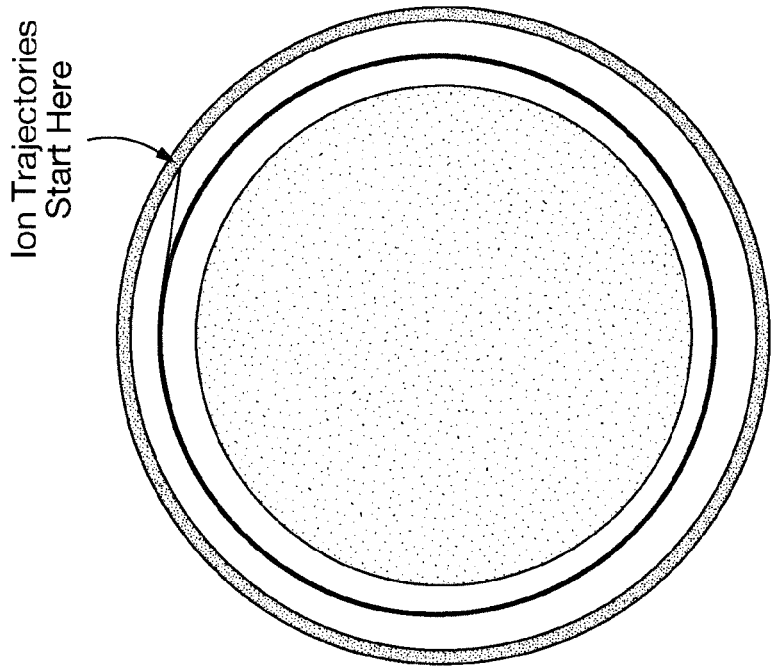
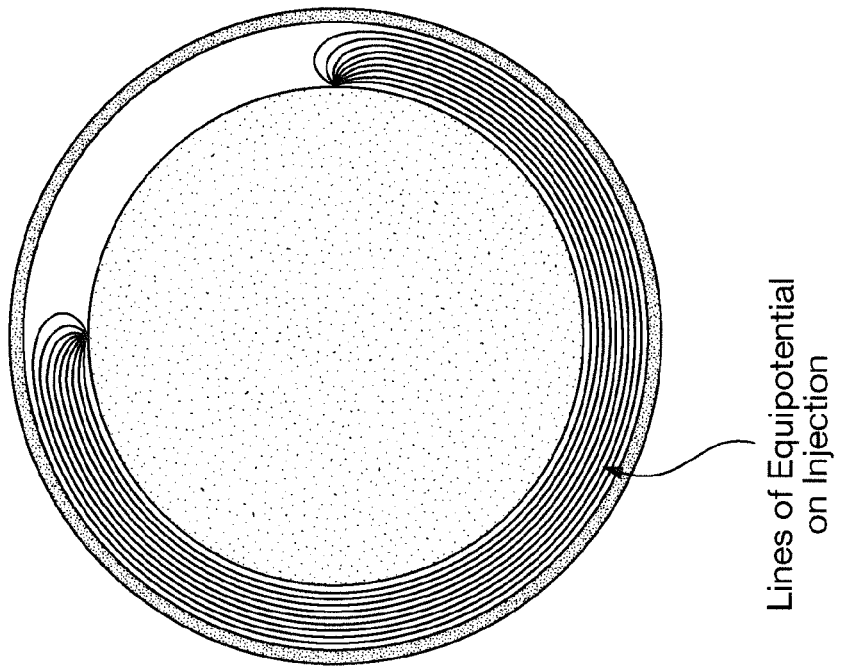

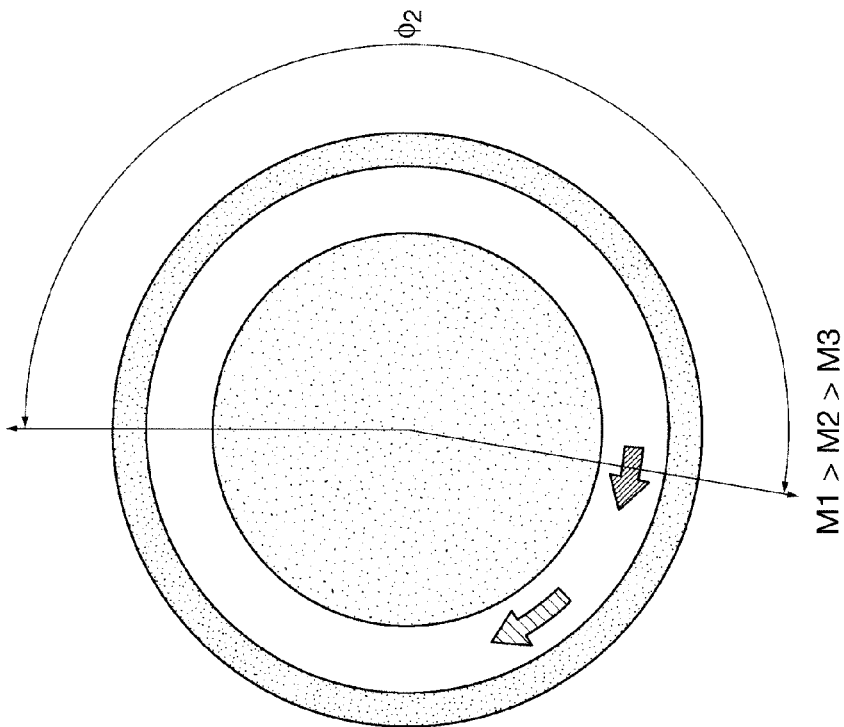
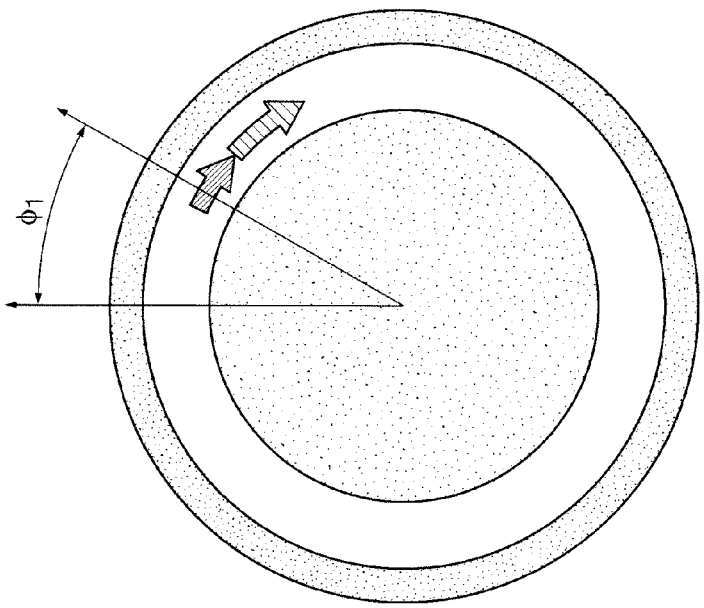

ORTHOGONAL ACCELERATION COAXIAL CYLINDER TIME OF FLIGHT MASS ANALYSER

CROSS-REFERENCE TO RELATED APPLICATION

This application is the National Stage of International Application No. PCT/GB2013/051269, filed 16 May 2013, which claims priority from and the benefit of U.S. Provisional Patent Application Ser. No. 61/650,008 filed on 22 May 2012, European Patent Application No. 12168612.5 filed on 21 May 2012, United Kingdom Patent Application No. 1208847.2 filed on 18 May 2012, United Kingdom Patent Application No. 1216489.3 filed on 14 Sep. 2012, United Kingdom Patent Application No. 1216488.5 filed on 14 Sep. 2012 and United Kingdom Patent Application No. 1216486.9 filed on 14 Sep. 2012. The entire contents of these applications are incorporated herein by reference.

BACKGROUND OF THE PRESENT INVENTION

The present invention relates to a Time of Flight mass analyser, a mass spectrometer, a method of mass analysing ions and a method of mass spectrometry.

Reference is made to W. C. Wiley, I. H. McLaren, "Time-of-Flight Mass Spectrometer with Improved Resolution" Review of Scientific Instruments 26, 1150 (1955) which sets out the basic equations that describe two stage extraction Time-of-Flight mass spectrometers. The principles apply equally to continuous axial extraction Time of Flight mass analysers, orthogonal acceleration Time of Flight mass analysers and time lag focussing instruments.

FIG. 1 shows the principle of spatial (or space) focussing whereby ions with an initial spatial distribution are brought to a focus at the plane of a detector so improving instrumental resolution.

The ion velocity and positional distributions are represented as phase space ellipses as shown in FIG. 2 which describe the condition of the ion beam as it traverses the instrument. A knowledge of the nature of phase space and Liouville's theorem is helpful to the understanding of various aspects of the preferred embodiment of the present invention.

A fundamental theorem in ion optics is Liouville's theorem which states that "For a cloud of moving particles, the particle density $\rho(x, p_x, y, p_y, z, p_z)$ in phase space is invariable.", wherein $p_x$, $p_y$, & $p_z$ are the momenta of the three Cartesian coordinate directions. Reference is made to "Geometrical Charged-Particle Optics", Harald H. Rose, Springer Series in Optical Sciences 142.

According to Liouville's theorem, a cloud of particles at a time $t_1$ that fills a certain volume in phase space may change its shape at a later time $t_n$ but not the magnitude of its volume. Attempts to reduce this volume by the use of electromagnetic fields is futile although it is of course possible to sample desired regions of phase space by aperturing the beam (rejecting un-focusable ions) before subsequent manipulation. A first order approximation splits Liouville's theorem into the three independent space coordinates x, y and z. The ion beam can now be described in terms of three independent phase space areas the shape of which change as the ion beam progresses through an ion optical system but not the total area itself. This concept is illustrated in FIG. 3 which shows an optical system comprising N optical elements with each element changing the shape of the phase space but not its area.

Ion distributions emanating from radio frequency ion guides containing buffer gases can typically be described in phase space distributions that are elliptical in shape. Such RF guides are commonly used to interface continuous ion beam sources such as Electrospray ionisation to Time of Flight mass analyser mass spectrometers. So it is the goal of the Time of Flight mass analyser designer to utilise the concept of spatial focussing to manipulate the initial ion beam represented by a phase space ellipse with large spatial distribution into one with a small distribution at the plane of the detector. Small spatial distributions at the detector plane coupled with long flight times make for high resolution Time of Flight mass analyser spectrometers. It is desired that the detector plane be isochronous for any particular mass to charge ratio. Generally Time of Flight mass analyser instruments disperse in mass to charge ratio according to the square of the time of flight (i.e. square root of mass to charge ratio is proportional to time). However, it is true that any ion (regardless of mass to charge ratio) when accelerated through any general electrostatic system of optical elements will take the same trajectory. So that an orthogonal acceleration Time of Flight mass analyser which may be considered to consist substantially of electrostatic elements, will bring ions of different mass to charge ratios into spatial focus at the same positions in the spectrometer but at different times.

The isochronous plane may be defined as being a plane in the spectrometer where ions of a unique mass to charge ratio have the same time of flight which is substantially independent of their initial phase space distribution, and it is at such a plane where an ion detector is sited for highest resolution. There are secondary effects which must be considered that make the Time of Flight mass analyser deviate from the ideal mass to charge ratio independent electrostatic system such as the finite rise time of the pusher, mass dependent phase space characteristics of ions emanating from RF devices, and the relative timing of pulsed ion packets and pulsed electric fields. These effects and the deviations from the ideal electrostatic system will be explained and discussed as they become relevant to the present invention.

The angle of inclination of the ellipse represents a correlated position/velocity distribution. An ellipse which has a large spatial extent and gentle inclination may be created by ion beams emanating from RF guides that have been accelerated through transfer optics into the pusher (acceleration) region of an orthogonal Time of Flight mass analyser. Where the ellipse is of a vertical orientation (tall and thin) we have an isochronous plane where it may be possible to site an ion detector. The shape of the ellipses at different positions in the spectrometer as the ion beam traverses the instrument are presented in the following diagrams describing the invention. It should be understood that no scale is given to either the velocity or position axes of the ellipses and that they are for illustrative purposes to understand the principles underlying the operation of the invention only.

The simple two stage Wiley McLaren Time of Flight mass analyser as shown in FIG. 1 is created by defining three distinct regions bounded by four principal planes P1, P2, P3, P4. The different field regions are typically created by placing arrays of grid wires or meshes (known hereafter as grids) at the positions of the principal planes each of which has a potential (voltage) which may be static or pulsed in nature applied to it. Acceleration and deceleration regions are visualised by inclined planes or curves along which the ions can be considered to roll without friction. Note that this gravitational analogy is not completely correct in that ions experience forces in proportion to their charge in electrostatics and so ions of similar charge but different mass accelerate at rates inversely proportion to their mass (whereas in gravity the force is proportion to mass so all particles accelerate at the same rate regardless of mass).

Each time the ion beam passes through a grid ions are lost due to collisions with the grid wires and are also deflected by electric field variations that exist in close proximity to the boundary due to the different field strengths between the two adjacent regions (known as scattering). So as the beam traverses the spectrometer it gets weaker due to these losses and also defocusing (divergence) of the ion beam due to its initial velocity spread.

A voltage pulse Vp is applied to the pusher plate at P1 creating an orthogonal acceleration field extract a portion of the beam into the Time of Flight mass analyser. It is the timing of the application of this voltage pulse that serves as the start time for the Time of Flight mass analyser. All the ions of interest (different mass to charge ratios) are allowed to fly to the detector before the pusher can fire again. The duty cycle of the sampling of the incoming ion beam is typically around 20% to allow an undistorted beam to be extracted, and this figure falls off in inverse proportion to the square root of mass. It is advantageous to retain the initial (pre push) velocity of the ions so that the resulting flight path of the ions is at an angle to the flight tube created by a vector between the two velocities, i.e. that of the incoming beam and that imparted by the spectrometer fields. This resulting vectorial trajectory enables placement of the ion detector offset to the pusher region which is advantageous for simplicity of construction as will be explained more fully later on. Resolutions of around 5000 can be achieved for state of the art instruments employing this type of geometry for a flight length of up to one meter.

Higher resolutions can be achieved in orthogonal acceleration Time of Flight mass spectrometers by reflecting the ion beam back on itself using a reflectron. Such a device can be adjusted to give an isochronous plane in a field free region ("FFR") while maintaining a compact instrument geometry. With prudent adjustment of the voltages this process can be repeated multiple times to increase the effective flight length (and hence flight time of the ions) of the instrument while maintaining the existence of an isochronous plane in the field free region.

FIG. 4 shows an arrangement wherein ions are accelerated by a two stage acceleration region defined by planes P1, P2, P3 and enter a field free region (P3 to P4). The ions then traverse the reflectron defined by planes P4, P5, P6 before returning through the field free region to a small mirror defined by planes P3, P7. The ion beam is sent back to the main reflectron after which it is sent back through the field free region at the end of which is placed an ion detector at the position of the isochronous plane namely P3.

The vectorial trajectory whereby the beam retains its initial component of direction of motion enables the ion detector to be placed adjacent to the pusher region. Resolutions as high as 50,000 to 100,000 are achievable with such a geometry but this performance comes at a cost to sensitivity (ion transmission). In this case the ion beam passes through grids 12 times, attenuating the beam on each pass.

In addition to this loss, the ion beam is diverging due its initial velocity spread and the scattering due to the fields in proximity to the grids, so its cross section has increased dramatically at the ion detector plane. When these factors along with the finite duty cycle of the instrument are all factored in, transmission may be as low as 1% of the initial beam intensity therefore reducing the sensitivity of the instrument.

WO 2005/040785 (Farnsworth) discloses a modified Spiratron arrangement wherein ions are introduced into the analyser using a pulsed electric field applied to a third sector electrode 155 as shown in FIG. 5. A packet of ions is sent into a pair of coaxial cylinders at an angle θ as shown in FIG. 6 where they undergo a helical trajectory 175 until they are ejected to an ion detector which is located external to the guide (as is apparent from FIG. 3 wherein the ion detector 70 is shown located outside of the flight tube). Ions attain stable trajectories by virtue of a pulsed voltage being applied to a third electrode. There is no disclosure of how to get ions out of the device once they are in the flight tube at the detector end.

It is noted that page 9, lines 9-10 implies a T/ΔT of 1000 (1 kHz repetition rate with 1 μs injection pulses) giving a maximum attainable resolution of 500. The low resolution is due to the fact that the disclosed arrangement imparts only first order energy (or spatial) focussing characteristic to the ion packet in the radial dimension.

It is noted that page 9, lines 11-18 contemplates an arrangement using a continuous Electrospray ion source wherein an upstream trap 90 may not be provided. It is suggested that according to this arrangement ions may be injected at θ=0° and the application of a voltage pulse to impart an axial drift velocity to the ions is delayed. This arrangement is also described on page 15, lines 5-15.

It will be understood by those skilled in the art that if a beam of ions is injected into the arrangement disclosed in WO 2005/040785 at θ=0° then in the context of the modified Spiratron arrangement disclosed therein the ions would need to be restricted from making a full rotation before an axial field was applied. Importantly, ions injected into the annular region disclosed in WO 2005/040785 would assume different rotational positions dependent upon their mass to charge ratio. Accordingly, ions having a relatively low mass to charge ratio might make nearly one rotation by the time that the axial field was applied whereas ions having a relatively high mass to charge ratio would make only a fraction of one rotation by the time that the axial field is applied.

Allowing a delay between ion injection and orthogonal acceleration would therefore result in ions having a mass dependent starting position such that the resolution of the mass analyser would be reduced even further.

With reference to FIG. 3 of WO 2005/040785 it is apparent that a port is provided between the annular region and the ion detector 70 through which ions must pass in order to be detected by the ion detector. Since ions would have a starting position which is mass dependent at the time that the axial field is applied, then ions having different masses would follow different helical paths through the annular region. As a result, some ions will follow helical trajectories which would miss the extraction port and hence not be detected by the ion detector.

The modified Spiratron arrangement disclosed in WO 2005/040785 would therefore also have a severe mass range limitation.

GB-2390935 (Verentchikov) discloses an arrangement as shown in FIG. 14 which comprises two Time of Flight mass spectrometers. Parent ions are separated in a first slow (and long) time of flight mass spectrometer (TOF1) which operates at low ion energies (1 to 100 eV) and fragment ions are subsequently mass analysed in a second fast and short time of flight mass spectrometer (TOF2) operating at much higher keV energy. Ions are injected into the first time of flight mass spectrometer TOF1 at an angle of inclination relative to the axis of two electrodes so that ions follow helical paths. It will be understood by those skilled in the art that the ions are not orthogonally accelerated into an annular ion guiding region. It is also apparent that the resolution of the arrangement disclosed in FIG. 14 is very low (R~75).

It is desired to provide a high resolution, high transmission orthogonal acceleration Time of Flight mass analyser which is compact in size.

SUMMARY OF THE PRESENT INVENTION

According to an aspect of the present invention there is provided a Time of Flight mass analyser comprising:

an annular ion guide having a longitudinal axis and comprising a first annular ion guide section and a second annular ion guide section;

a first device arranged and adapted to introduce ions into the first annular ion guide section so that the ions form substantially stable circular orbits within the first annular ion guide section about the longitudinal axis;

an ion detector disposed within the annular ion guide;

a second device arranged and adapted to orthogonally accelerate ions in a first axial direction from the first annular ion guide section into the second annular ion guide section; and a third device arranged and adapted to maintain an axial DC potential along at least a portion of the second annular ion guide section so that the ions are reflected in a second axial direction which is substantially opposed to the first axial direction and so that the ions undergo multiple axial passes through the second annular ion guide section before being detected by the ion detector.

The arrangements disclosed in WO 2005/040785 (Farnsworth) comprise modified Spiratron arrangements wherein ions follow helical orbits.

WO 2005/040785 does not disclose causing ions to form substantially stable circular orbits within an annular ion guide section about the longitudinal axis prior to being orthogonally accelerated.

WO 2005/040785 does not disclose an ion detector disposed within the annular ion guide. With reference to FIG. 3 of WO 2005/040785 it is apparent that the ion detector is not located within the annular ion guide and furthermore the ion detecting surface of the ion detector 70 is arranged in a plane which is parallel to the longitudinal axis rather than being substantially perpendicular to the longitudinal axis.

WO 2005/040785 does not disclose maintaining an axial DC potential along at least a portion of the annular ion guide section so that the ions are reflected in a second axial direction which is substantially opposed to the first axial direction and so that the ions undergo multiple axial passes through the annular ion guide.

It will therefore be appreciated that the modified Spiratron arrangement disclosed in WO 2005/040785 operates in a fundamentally different manner to the present invention.

In the arrangement disclosed in WO 2005/040785 ions are accelerated in the flight tube and experience time of flight dispersion in a helical direction i.e. time of flight dispersion is in both a longitudinal and a rotational direction.

In contrast, according to the present invention time of flight dispersion occurs only in a longitudinal direction.

Ions which are orthogonally accelerated are arranged to be spatially focused to an isochronous plane which is substantially perpendicular to the longitudinal axis.

This is in contrast to the modified Spiratron arrangement disclosed in WO 2005/040785 wherein the isochronous plane is parallel to the longitudinal axis.

The ion detecting surface of the ion detector is preferably positioned substantially at the isochronous plane.

The second device is preferably arranged and adapted to apply a pulsed axial electric field.

The second device is preferably arranged and adapted to apply a pulsed radial electric field at substantially the same time as the pulsed axial electric field. The second device is preferably arranged and adapted to apply a pulsed radial electric field at substantially the same time as the pulsed axial electric field so that the ions assume non-circular or elliptical orbits in a plane perpendicular to the longitudinal axis.

WO 2005/040785 does not teach or suggest applying a pulsed radial electric field at the same time as applying a pulsed axial electric field so that looking down the length of the annular ion guiding region ions assume elliptical rather than circular paths.

The second device is preferably arranged and adapted to orthogonally accelerate the ions into the second annular ion guide section so that the ions temporally separate according to their mass to charge ratio.

The second device is arranged and adapted to orthogonally accelerate the ions so that time of flight dispersion occurs only in a longitudinal direction.

Time of flight dispersion solely in a longitudinal direction represents a significant distinction of the present invention over known Spiratron arrangements such as the arrangement disclosed in WO 2005/040785 wherein time of flight dispersion is in a helical direction.

Furthermore, according to the present invention the detecting surface of the ion detector is arranged in a plane which is orthogonal or perpendicular to the longitudinal axis. This is because the isochronous plane of ions according to the present invention is substantially perpendicular to the isochronous plane of ions in the arrangements disclosed in WO 2005/040785.

The ion detector preferably has an annular, part annular or segmented annular ion detecting surface.

Such an arrangement is not disclosed in WO 2005/040785.

According to the preferred embodiment the ion detector is located either: (i) substantially in the centre of the annular ion guide or the second annular ion guide section; (ii) substantially at an end of the annular ion guide or the second annular ion guide section; (iii) at an end of a field free region; (iv) adjacent the first annular ion guide section; or (v) distal to the first annular ion guide section.

The annular ion guide preferably comprises an inner cylindrical electrode arrangement.

The inner cylindrical electrode arrangement is preferably axially segmented and comprises a plurality of first electrodes.

The annular ion guide preferably comprises an outer cylindrical electrode arrangement.

The outer cylindrical electrode arrangement is preferably axially segmented and comprises a plurality of second electrodes.

According to the preferred embodiment an annular time of flight ion guiding region is formed between the inner cylindrical electrode arrangement and the outer cylindrical electrode arrangement.

The Time of Flight mass analyser preferably further comprises a device arranged and adapted to apply DC potentials to the inner cylindrical electrode arrangement and/or the outer cylindrical electrode arrangement in order to maintain a radial DC potential which acts to confine ions radially within the annular ion guide.

The Time of Flight mass analyser preferably further comprises a control system arranged and adapted:

(i) to apply one or more first voltages to one or more of the first electrodes and/or the second electrodes so that ions located in the first annular ion guide section precess or move in orbits about the inner cylindrical electrode arrangement; and then (ii) to apply one or more second voltages to one or more of the first electrodes and/or the second electrodes so that ions are orthogonally accelerated into the second annular ion guide section so that ions pass along spiral paths through the second annular ion guide section in a first axial direction;

(iii) optionally to apply one or more third voltages to one or more of the first electrodes and/or the second electrodes so that ions are reflected back in a second axial direction which is opposed to the first axial direction; and (iv) to determine the time of flight of ions passing through the annular ion guide or the second annular ion guide section.

The second device is preferably arranged and adapted to apply a potential difference across the first annular ion guide section so that ions are orthogonally accelerated out of the first annular ion guide section and pass into the second annular ion guide section.

Ions preferably follow substantially spiral paths as they pass through the second annular ion guide section. The spiral paths are preferably non-helical along at least a portion of the annular ion guide or the second annular ion guide section such that the ratio of curvature to torsion of the spiral paths varies or is non-constant.

This is in contrast to the modified Spiratron arrangement disclosed in WO 2005/040785 wherein ions follow helical paths such that the ratio of curvature to torsion of the ion paths remains constant.

The Time of Flight mass analyser preferably further comprises a device arranged and adapted to maintain one or more half-parabolic or other DC potentials along a portion of the annular ion guide or the second annular ion guide section in order to reflect ions.

Such an arrangement is not disclosed in WO 2005/040785.

The Time of Flight mass analyser preferably further comprises a device arranged and adapted to maintain one or more parabolic DC potentials along a portion of the annular ion guide or the second annular ion guide section so that ions undergo simple harmonic motion.

Such an arrangement is not disclosed in WO 2005/040785.

The annular ion guide or the second annular ion guide section preferably comprises one or more reflectrons for reflecting ions in a reverse axial direction.

Such an arrangement is not disclosed in WO 2005/040785.

The second device is preferably arranged to orthogonally accelerate ions at a time $T_1$ and wherein the ions are detected by the ion detector at a subsequent time $T_2$ and wherein ions having a mass to charge ratio in the range<100, 100-200, 200-300, 300-400, 400-500, 500-600, 600-700, 700-800, 800-900 or 900-1000 are arranged to have a total time of flight $T_2-T_1$ through the annular ion guide or the second annular ion guide section selected from the group consisting of: (i) <50 µs; (ii) 50-100 µs; (iii) 100-150 µs; (iv) 150-200 µs; (v) 200-250 µs; (vi) 250-300 µs; (vii) 300-350 µs; (viii) 350-400 µs; (ix) 400-450 µs; (x) 450-500 µs; and (xi) >500 µs.

Ions having different mass to charge ratios follow substantially different spiral paths through the annular ion guide or the second annular ion guide section.

This is in contrast to a Spiratron arrangement as disclosed, for example, in WO 2005/040785 wherein ions having different mass to charge ratios follow essentially the same helical path since the ions experience time of flight dispersion in the helical direction.

According to a preferred embodiment electrodes in the first annular ion guide section are segmented so that at least a first electric field sector and a second electric field sector are formed in use.

The Time of Flight mass analyser preferably further comprises a control system arranged and adapted at a first time T1 to inject ions substantially tangentially into the first electric field sector whilst maintaining a substantially zero radial electric field in the first electric field sector so that the ions experience a substantially field free region whilst being injected into the first annular ion guide section.

The control system is preferably further arranged and adapted to maintain a radial electric field in the second electric field sector so that at a second later time T2 ions pass from the first electric field sector into the second electric field sector and become radially confined.

The control system is preferably further arranged and adapted at a third time T3, wherein T3>T1, to cause a radial electric field to be maintained in the first electric field sector so that as ions pass from the second electric field sector into the first electric field sector the ions continue to be radially confined and form substantially stable circular orbits within the first annular ion guide section.

The second device is preferably arranged and adapted to orthogonally accelerate ions from the first annular ion guide section into the second annular ion guide section at a fourth time T4, wherein T4>T3.

The Time of Flight mass analyser comprises a control system arranged and adapted to determine the time of flight of the ions orthogonally accelerated from the first annular ion guide section into the second annular ion guide section.

The ion detector is preferably arranged and adapted to detect ions impacting or impinging upon an ion detection surface of the ion detector.

According to an aspect of the present invention there is provided a mass spectrometer comprising a Time of Flight mass analyser as described above.

According to an aspect of the present invention there is provided a method of mass analysing ions comprising:

providing an annular ion guide having a longitudinal axis and comprising a first annular ion guide section and a second annular ion guide section;

introducing ions into said first annular ion guide section so that said ions form substantially stable circular orbits within said first annular ion guide section about said longitudinal axis;

providing an ion detector disposed within said annular ion guide;

orthogonally accelerating ions in a first axial direction from said first annular ion guide section into said second annular ion guide section; and maintaining an axial DC potential along at least a portion of said second annular ion guide section so that said ions are reflected in a second axial direction which is substantially opposed to said first axial direction and so that said ions undergo multiple axial passes through said second annular ion guide section before being detected by said ion detector.

According to an aspect of the present invention there is provided a method of mass spectrometry comprising a method of mass analysing ions as described above.

According to an aspect of the present invention there is provided a Time of Flight mass analyser comprising:
an annular ion guide having a longitudinal axis;
a device arranged and adapted to maintain an axial DC potential along at least a portion of said annular ion guide; and
a device arranged and adapted to orthogonally accelerate ions into said annular ion guide such that said ions become temporally separated and make multiple axial passes and wherein time of flight dispersion occurs only in a longitudinal direction.

Such an arrangement is not disclosed in WO 2005/040785. According to the arrangement disclosed in WO 2005/040785 time of flight dispersion is in the helical direction i.e. the time of flight dispersion does not occur only or solely in the longitudinal direction. Furthermore, WO 2005/040785 does not disclose maintaining an axial DC potential along a portion of the annular ion guide or causing the ions to make multiple axial passes.

According to an aspect of the present invention there is provided a method of mass analysing ions comprising:
providing an annular ion guide having a longitudinal axis;
maintaining an axial DC potential along at least a portion of said annular ion guide; and
orthogonally accelerating ions into said annular ion guide such that said ions become temporally separated and make multiple axial passes and wherein time of flight dispersion occurs only in a longitudinal direction.

Such an arrangement is not disclosed in WO 2005/040785. According to the arrangement disclosed in WO 2005/040785 time of flight dispersion is in the helical direction i.e. the time of flight dispersion does not occur only or solely in the longitudinal direction. Furthermore, WO 2005/040785 does not disclose maintaining an axial DC potential along a portion of the annular ion guide or causing the ions to make multiple axial passes.

According to an aspect of the present invention there is provided a Time of Flight mass analyser comprising:
an annular ion guide having a longitudinal axis; and
a device arranged and adapted to orthogonally accelerate ions into the annular ion guide so that the ions make multiple axial passes and wherein the ions are spatially focused to an isochronous plane which is substantially perpendicular to the longitudinal axis.

This is in contrast to the arrangement disclosed in WO 2005/040785 wherein the isochronous plane is parallel to the longitudinal axis and wherein ions do not make multiple axial passes.

According to an aspect of the present invention there is provided a method of mass analysing ions comprising:
providing an annular ion guide having a longitudinal axis; and
orthogonally accelerating ions into said annular ion guide so that said ions make multiple axial passes and spatially focusing said ions to an isochronous plane which is substantially perpendicular to said longitudinal axis.

This is in contrast to the arrangement disclosed in WO 2005/040785 wherein the isochronous plane is parallel to the longitudinal axis and wherein ions do not make multiple axial passes.

According to an aspect of the present invention there is provided a Time of Flight mass analyser comprising:
an annular ion guiding region; and
a first device arranged and adapted to orthogonally accelerate ions into the annular ion guiding region.

A person skilled in the art will appreciate that with known Spiratron arrangements ions follow a helical path. In contrast to such known arrangements, the path taken by ions according to the preferred embodiment is not substantially helical. It will be appreciated that a curve is called a general helix if and only if the ratio of curvature to torsion is constant. According to the preferred embodiment ions do not make uniform rotations along the axial direction.

The Time of Flight mass analyser preferably further comprises a first cylindrical electrode arrangement.

The first cylindrical electrode arrangement is preferably axially segmented and comprises a plurality of first electrodes.

The Time of Flight mass analyser preferably further comprises a second cylindrical electrode arrangement.

The second cylindrical electrode arrangement is preferably axially segmented and comprises a plurality of second electrodes.

The annular ion guiding region is preferably formed between the first cylindrical electrode arrangement and the second cylindrical electrode arrangement.

In a first mode of operation ions preferably precess or move in orbits within a first portion of the annular ion guiding region.

The first device is preferably arranged and adapted to apply a potential difference across a first portion of the annular ion guiding region so that ions are orthogonally accelerated out of the first portion of the annular ion guiding region and pass into a second portion of the annular ion guiding region.

Ions preferably undergo one or more orbits and/or follow helical paths as they pass through the second portion of the annular ion guiding region.

The Time of Flight mass analyser preferably further comprises an ion detector.

The ion detector is preferably located within or adjacent the annular ion guiding region.

The ion detector preferably has an annular ion detecting surface.

The ion detector is preferably located in the centre of the annular ion guiding region.

The ion detector is preferably located at the end of a field free region and/or at an end of the annular ion guiding region.

The ion detector is preferably located adjacent the first portion of the annular ion guiding region.

The ion detector is preferably located distal to the first portion of the annular ion guiding region.

The Time of Flight mass analyser preferably further comprises a device arranged and adapted to maintain one or more half-parabolic or other potentials along a portion of the annular ion guiding region in order to reflect ions.

The Time of Flight mass analyser preferably further comprises a device arranged and adapted to maintain one or more parabolic potentials along a portion of the annular ion guiding region so that ions undergo simple harmonic motion.

The annular ion guiding region preferably comprises one or more reflectrons for reflecting ions in a reverse axial direction.

Ions are preferably orthogonally accelerated at a time T1 and are detected at a time T2 and wherein ions having a mass to charge ratio in the range<100, 100-200, 200-300, 300-400, 400-500, 500-600, 600-700, 700-800, 800-900 or 900-

1000 are arranged to have a total time of flight T2-T1 through the annular ion guiding region selected from the group consisting of: (i) <50 μs; (ii) 50-100 μs; (iii) 100-150 μs; (iv) 150-200 μs; (v) 200-250 μs; (vi) 250-300 μs; (vii) 300-350 μs; (viii) 350-400 μs; (ix) 400-450 μs; (x) 450-500 μs; and (xi)>500 μs.

According to an aspect of the present invention there is provided a mass spectrometer comprising a Time of Flight mass analyser as described above.

According to an aspect of the present invention there is provided a method of mass analysing ions comprising:

orthogonally accelerating ions into an annular ion guiding region; and determining the time of flight of the ions.

According to an aspect of the present invention there is provided a method of mass spectrometry comprising a method of mass analysing ions as described above.

According to an aspect of the present invention there is provided a Time of Flight mass analyser comprising:

an inner cylindrical electrode arrangement comprising a plurality of first electrodes and an outer cylindrical electrode arrangement comprising a plurality of second electrodes, wherein the outer cylindrical arrangement is arranged about the inner cylindrical electrode so as to form, in use, an annular ion guiding region between the inner and outer electrodes;

an ion detector disposed within or at an end of the annular ion guiding region; and a control system arranged and adapted:

(i) to apply one or more first voltages to one or more of the first electrodes and/or the second electrodes so that ions are located in a first region of the annular ion guiding region, wherein ions precess or move in orbits about the inner cylindrical electrode arrangement; and then (ii) to apply one or more second voltages to one or more of the first electrodes and/or the second electrodes so that ions are orthogonally accelerated into a second region of the annular ion guiding region so that ions pass along helical or spiral paths through the second region of the annular ion guiding region in a first axial direction;

(iii) to apply one or more third voltages to one or more of the first electrodes and/or the second electrodes so that ions are reflected back in a second axial direction which is opposed to the first axial direction; and (iv) to determine the time of flight of ions passing through the annular ion guiding region.

According to an aspect of the present invention there is provided a method of mass analysing ions comprising:

causing ions to be located in a first region of an annular ion guiding region, wherein ions precess or move in orbits about an inner cylindrical electrode arrangement; and then orthogonally accelerating ions into a second region of the annular ion guiding region so that ions pass along helical or spiral paths through the second region of the annular ion guiding region in a first axial direction;

reflecting ions back in a second axial direction which is opposed to the first axial direction; and determining the time of flight of ions passing through the annular ion guiding region.

A disadvantage of known orthogonal acceleration Time of Flight mass analysers is that they suffer from transmission loss due to divergence of the ion beam in long flight path instruments resulting in overfilling of the available detector area. The divergence may arise from initial ion beam conditions or from scattering at the grid boundaries.

The preferred embodiment of the present invention seeks to overcome this limitation by confining ions in a stable radial orbit which is perpendicular to the direction of time of flight dispersion.

The preferred embodiment of the present invention has a number of advantages over conventional arrangements. The preferred embodiment, for example, has increased resolution over single pass devices.

According to an embodiment the preferred Time of Flight mass analyser also has high transmission in multipass mode due to gridless construction of repeating flight path elements.

Another advantage of the preferred embodiment is that it has high transmission due to stable radial confinement preventing overfilling of the detector (by divergence).

The preferred embodiment also has a high duty cycle of ion packets injected into instrument.

Another advantage of the preferred embodiment is that there is no use of external ion deflectors to align ions with the instrument optic axis. Such deflectors introduce aberrations and complexity of construction.

A further advantage of the preferred embodiment is increased entrance energy and consequential tolerance to surface charging of upstream components.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) one or more energy analysers or electrostatic energy analysers; and/or (h) one or more ion detectors; and/or (i) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (j) a device or ion gate for pulsing ions; and/or (k) a device for converting a substantially continuous ion beam into a pulsed ion beam.

The mass spectrometer may further comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

BRIEF DESCRIPTION OF THE DRAWINGS

Various embodiments of the present invention will now be described, by way of example only, and with reference to the accompanying drawings in which:

FIG. 6A shows ions confined in a stable orbit and FIG. 6B shows a pulsed voltage being applied to a grid which is placed inside the analyser between the two cylinders;

FIG. 7A shows an embodiment and FIG. 7B shows another embodiment of the present invention;

FIG. 8A shows an embodiment wherein ions are initially confined, FIG. 8B shows a parabolic potential being applied to one side of the ion path, FIG. 8C shows ions oscillating along a parabolic potential and FIG. 8D shows the ions being transmitted to an ion detector;

FIG. 9A shows ions being confined initially, FIG. 9B shows ions being orthogonally accelerated, FIG. 9E shows an embodiment wherein ions oscillate within a parabolic potential and FIG. 9F shows an embodiment wherein ions are transmitted to an ion detector located at the exit of a field free region;

FIG. 16A shows a preferred embodiment of the present invention in cross-section and shows an ion beam initially undergoing stable circular orbits prior to being orthogonally accelerated into an annular time of flight region.

FIG. 23A shows a preferred method of injecting ions into the annular ion guiding region by splitting the injection region into a first and second sector and ensuring that ions initially experience a field free region when they are injected into the first sector and FIG. 23B shows the resulting ion trajectories after ions have moved from the first sector into the second sector and a radial field is restored in the first sector; and FIG. 24A shows ions which have been injected into the mass analyser separating rotationally and FIG. 24B shows ions which have been injected into the mass analyser separating rotationally at a later time.

DETAILED DESCRIPTION OF PREFERRED EMBODIMENTS

Figure 5:
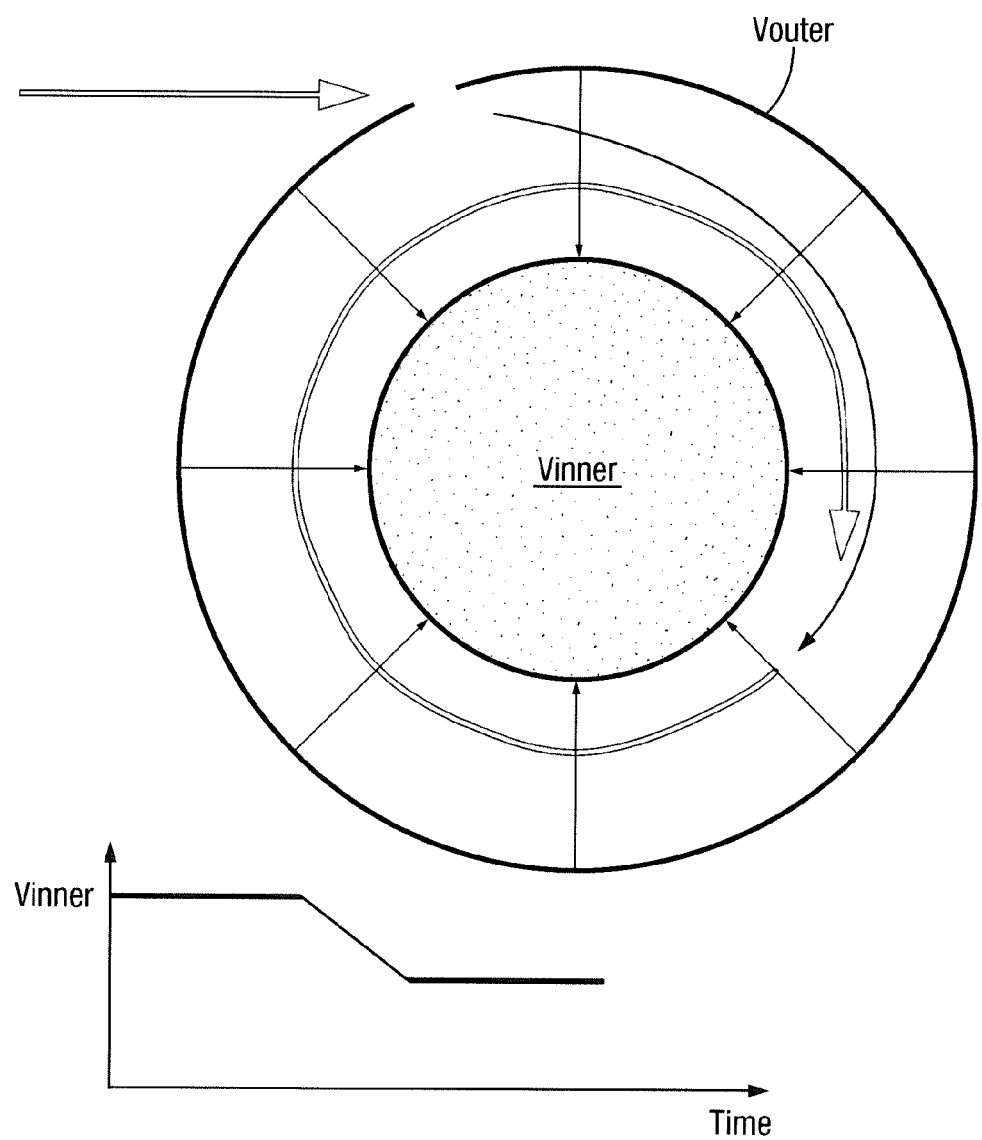
FIG. 5 shows an end view of a preferred Time of Flight mass analyser.

An arrangement will now be described with reference to FIG. 5. FIG. 5 shows an arrangement wherein a Time of Flight mass analyser is provided comprising two coaxial cylindrical electrodes with an annular ion guiding volume therebetween.

According to the preferred embodiment ions are confined radially between two coaxial cylinders which are held at different potentials Vouter and Vinner. The ion beam (which is preferably a packet of ions containing the different mass to charge ratio species to be analysed) is arranged to approach the outer cylinder where either a hole or a gap through which the ion beam may pass is preferably provided.

Ions entering the annular ion guiding volume preferably form stable circular orbits by increasing the field between the inner and outer cylinders once the ion beam has entered the device. In the absence of any other fields once inside the cylinders the ions preferably remain in orbit but will disperse in the axial direction according to their initial axial velocities. This is shown in FIG. 6A.

Referring now to FIG. 6B, once the ions are confined in stable circular orbits a pulsed voltage is applied to a grid electrode which is preferably placed inside the analyser between the two cylinders. In order to create the electric field functions required to achieve spatial focussing the inner and outer cylinders are preferably segmented and different voltages are preferably applied to each of the inner and outer segmented electrodes.

FIG. 6A shows how the inner and outer cylindrical electrodes may be axially segmented according to an embodiment. According to the preferred embodiment the inner and outer cylindrical electrodes are axially segmented in all of the embodiments described below, although for ease of illustration only some of the following drawings may omit the axial segmentation.

Referring again to FIG. 6B, the ions are orthogonally accelerated in an axial direction and preferably continue to rotate around the central electrode set but at the same time preferably begin to move along the axis of the Time of Flight mass analyser in a substantially helical manner.

It should be understood that time of flight dispersion only occurs in the axial direction and that the ions are confined radially to prevent transmission losses. As a result, the two coordinates in the preferred cylindrical device are decoupled in their behaviour.

Figure 1:
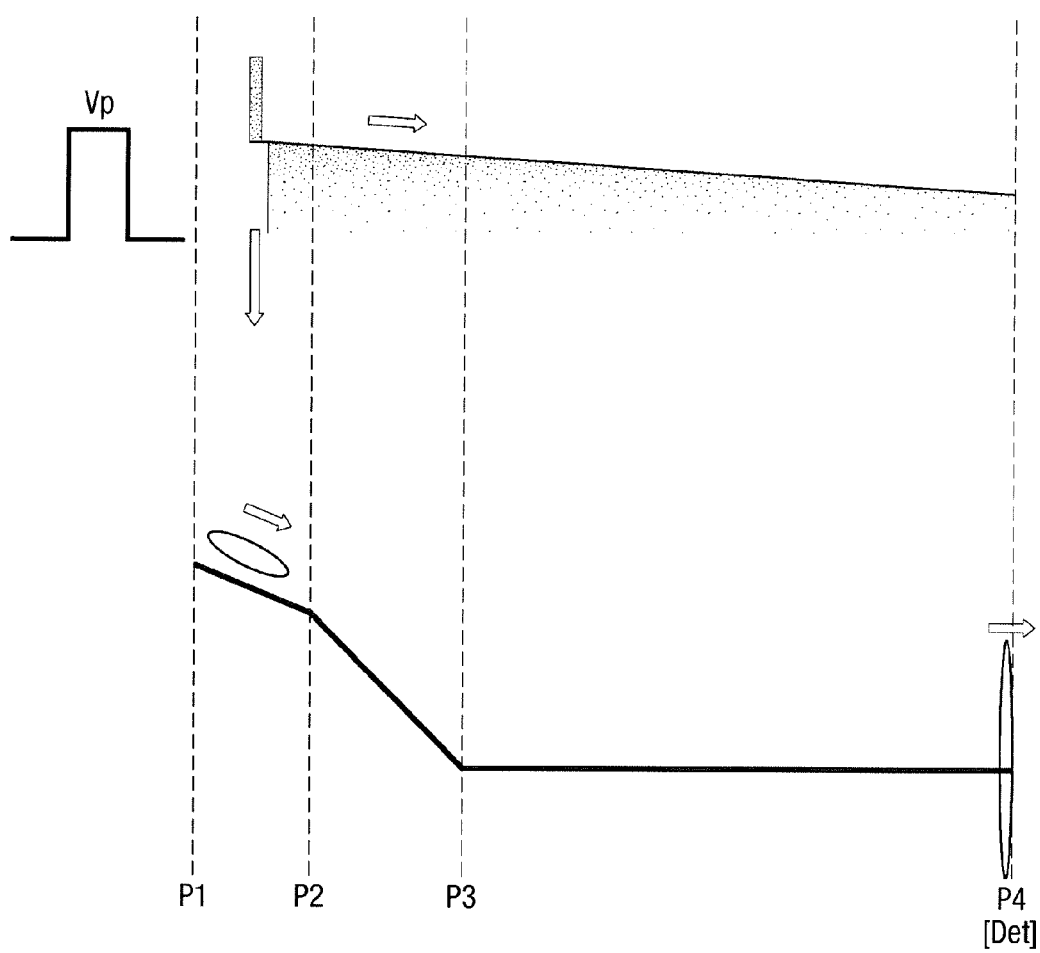
FIG. 1 shows the principle of spatial focusing.
Figure 2:
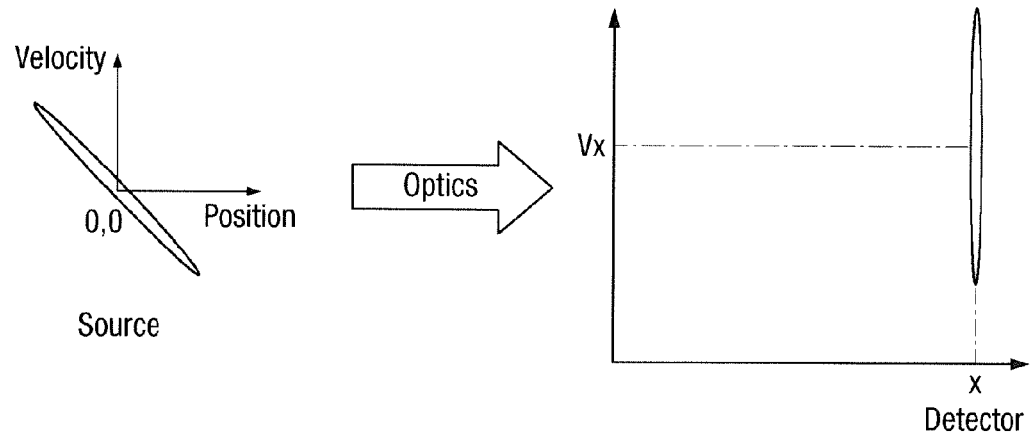
FIG. 2 shows ion velocity and phase space ellipses.
Figure 3:
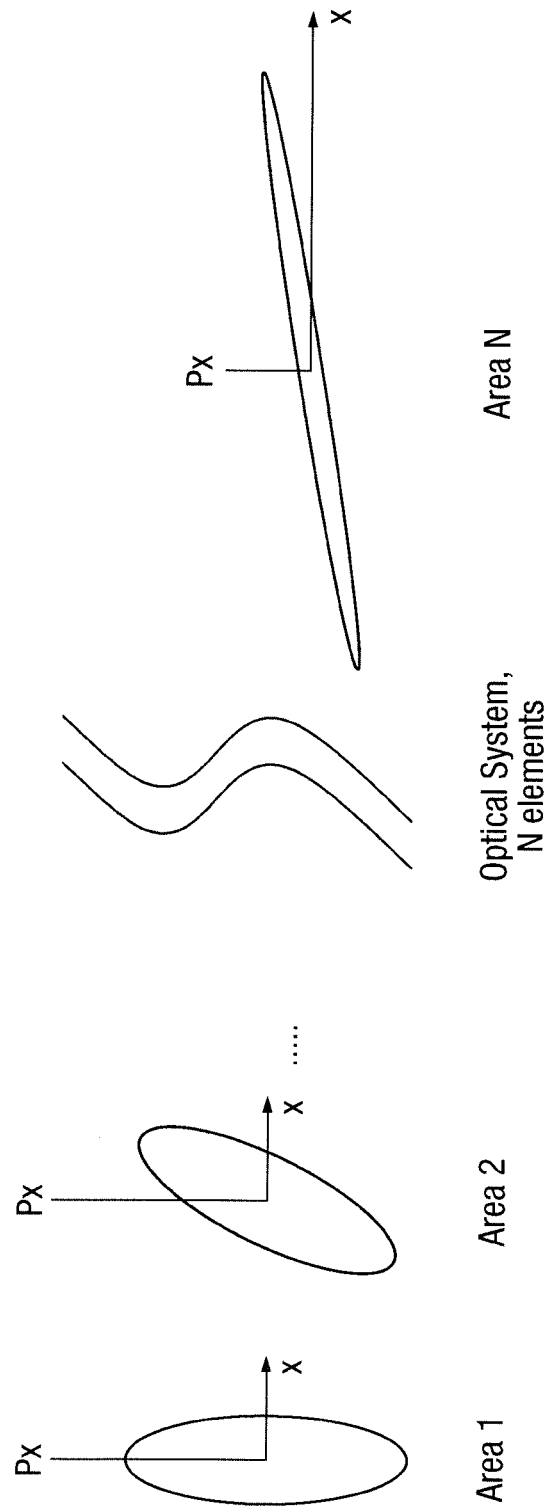
FIG. 3 illustrates Liouville's theorem.
Figure 4:
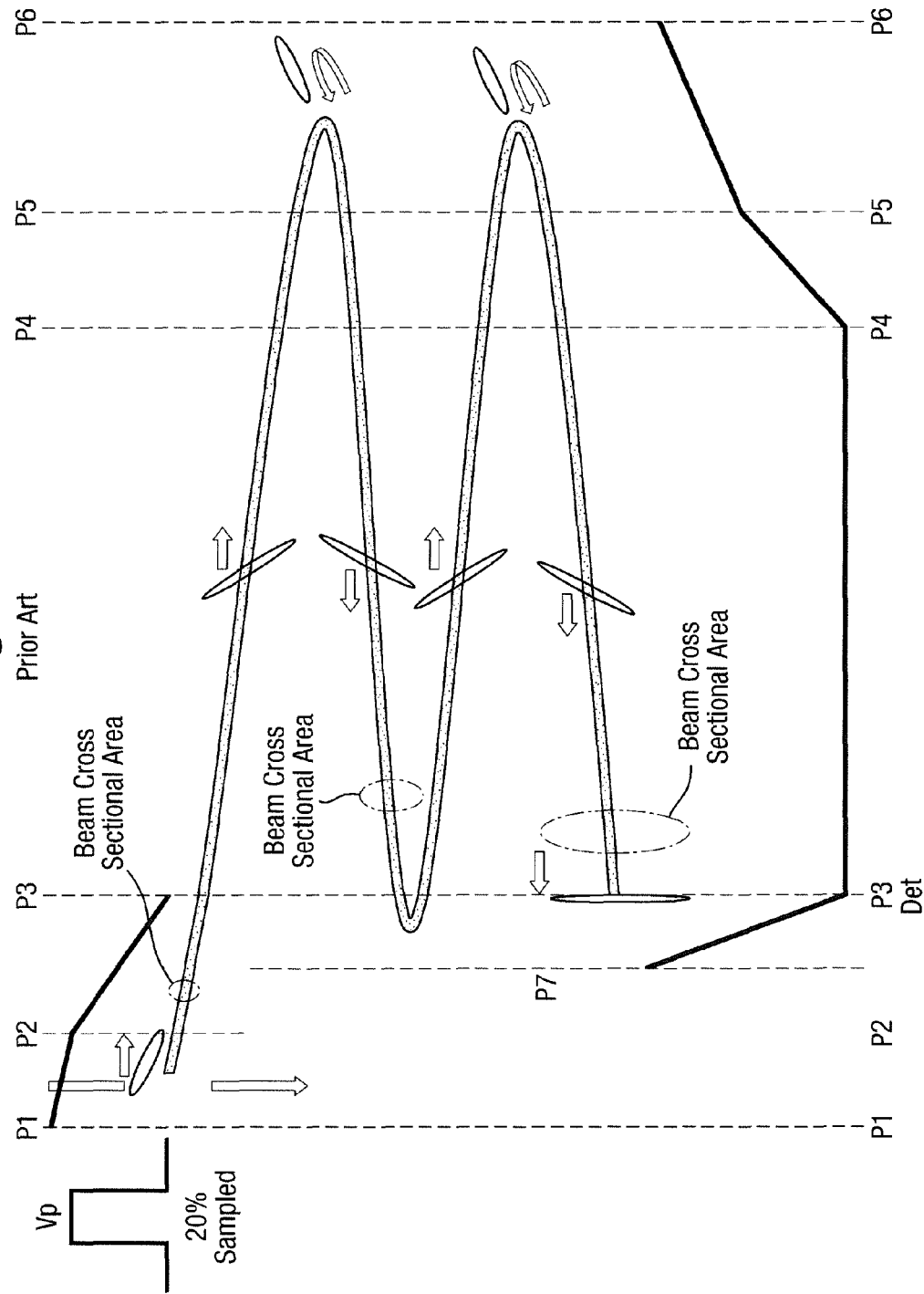
FIG. 4 shows a W-shaped Time of Flight region in a conventional Time of Flight mass analyser.

FIG. 6B illustrates a simple embodiment with four principal planes P1, P2, P3, P4 which are directly analogous to the principal planes in a Wiley McLaren Time of Flight mass analyser as shown in FIG. 1. Spatial focussing is achieved in the same principle. However, in the geometry according to the embodiment as shown in FIG. 6B, the stable orbits in the radial direction prevent losses due to beam divergence and grid scattering at the grid boundaries.

A further advantage of the geometry according to the preferred embodiment is that when coupled to a pulsed packet of ions incoming to the spectrometer the entire ion packet may be captured into a stable orbit and utilised. If ions are stored in an upstream RF device between spectrometer acquisition cycles (pushes) then essentially a 100% duty cycle is potentially achievable with the preferred geometry.

According to the embodiment shown in FIGS. 6A and 6B ions may still be lost due to collisions with grid electrodes but the preferred embodiment advantageously has substantially higher transmission than conventional arrangements.

Other embodiments are also contemplated and will be described below which do not utilise grid electrodes and which are therefore even more advantageous compared with conventional arrangements.

It should be noted that the application of an orthogonal acceleration electric field or pulsing electric field after stable radial orbits are achieved is an important distinction over other known forms of mass analysers.

In particular, an Orbitrap® mass analyser is known wherein a packet of ions from outside the device is pulsed into the mass analyser using deflection devices to change the direction of the beam to the axis of the spectrometer. Such deflection devices cause aberrations in the time of flight and distortions in the isochronous plane. These aberrations limit the resolution of such devices such that very long flight times are required before high resolutions can be achieved.

A particular advantage of the preferred embodiment is that the application of the acceleration field after stable orbits are achieved negates the need for deflection devices and enables resolution performances to be achieved in faster timescales similar to conventional orthogonal acceleration Time of Flight mass analysers.

It is an advantage of radially confined coaxial cylinder Time of Flight mass analysers according to embodiments of the present invention that long flight paths are possible without losses due to beam divergence losses. As such the preferred embodiment is ideally suited to multipass Time of Flight mass analyser geometries.

Various multipass geometries are contemplated and according to preferred embodiments contain a minimum number of grid electrodes in order to reduce losses at the principal planes.

FIGS. 7A and 7B show a preferred geometry according to an embodiment. According to this embodiment ions are injected and stabilised into one side of an axially symmetric device before a parabolic potential is applied along the length of the Time of Flight mass analyser. The parabolic potential acts to accelerate ions towards the centre of the spectrometer. The form of parabolic potential well preferably allows the ions to oscillate back and forth exhibiting simple harmonic motion. The more passes that the ions experience before detection the greater the resolution of the instrument.

Advantageously, ions may be stored in an upstream ion trap. Ions may be mass selectively ejected from the ion trap to sequentially release known mass ranges of ions to the analyser while storing others in the population. In this way a high resolution mass spectrum covering the entire mass range may stitched together from segments of the smaller acquired mass range.

The evolution of phase space illustrated in FIG. 7B shows that the isochronous plane is found in the centre of the device substantially at the bottom of the potential well. In fact there is a small deviation from the bottom which is a function of the inclination of the initial phase space ellipse but at typically envisaged device geometries this is a small effect.

According to an embodiment the ion detector may be placed or located in a region of the instrument where there is no axial field present.

According to an embodiment the ion detector may be located in an axial field free region of the instrument as will now be discussed with reference to FIGS. 8A-8D. FIGS. 8A-8D show an embodiment incorporating a combination of a Wiley McLaren and parabolic potential well sections. Each of FIGS. 8A-8D illustrate a different time in the acquisition cycle of the instrument.

Ions are preferably extracted from a coaxial geometry Time of Flight mass analyser according to an embodiment of the present invention and which incorporates a two field Wiley McLaren type source. The ions are orthogonally accelerated into a field free region and pass along through the field free region. The ions then experience a parabolic potential gradient (half a well) as shown in FIGS. 8A and 8B.

Figure 8C:
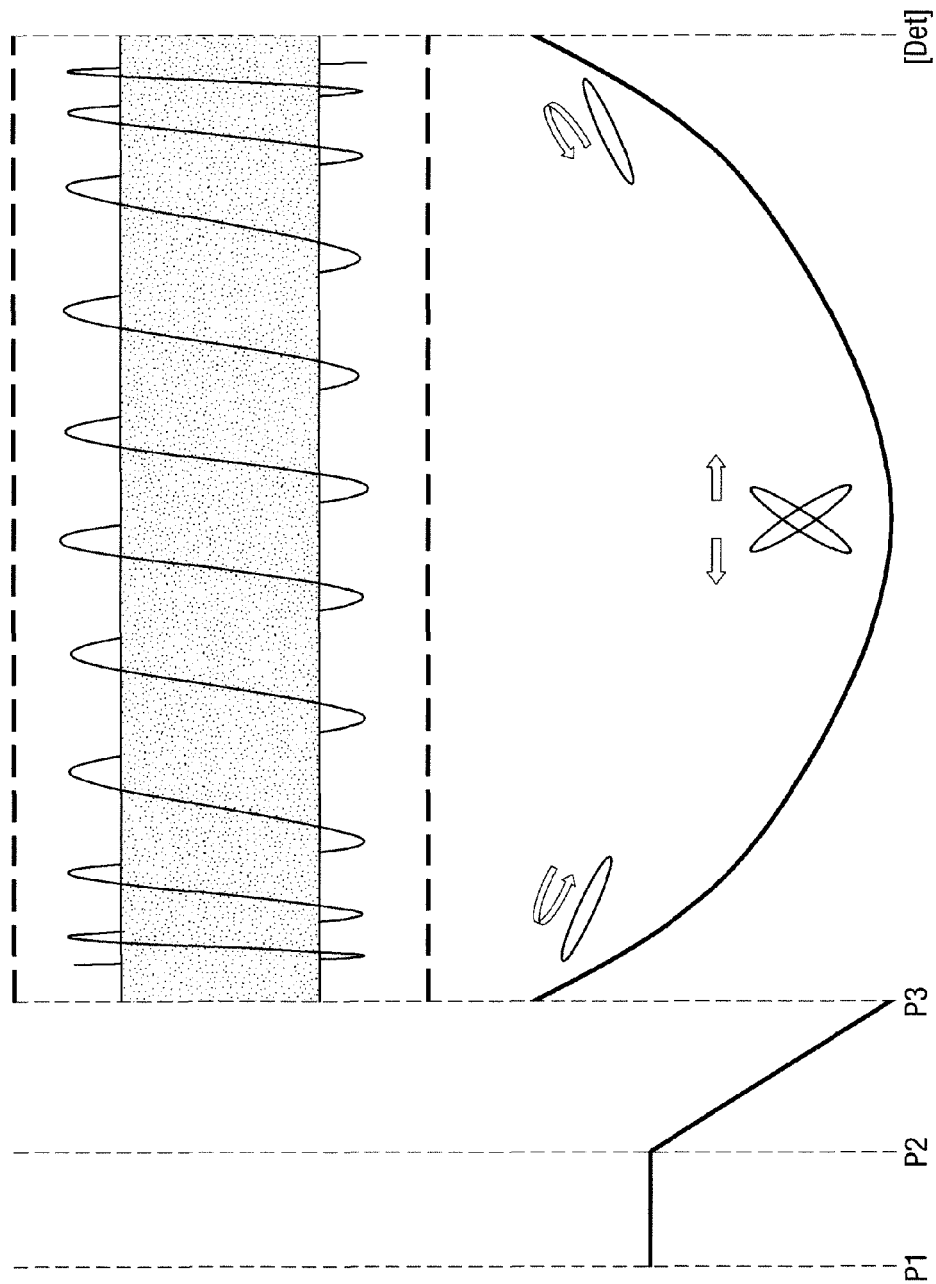

While ions are inside the parabolic section as shown in FIG. 8B, the other half of the well is preferably switched ON as shown in FIG. 8C and the ions are preferably allowed to oscillate for a desired number of times to increase the effective flight path of the instrument before ejection towards the ion detector as shown in FIG. 8D.

It will be noted from FIG. 8D that the isochronous plane is no longer at the base of the potential well. This is due to the amount of field free region required to bring the ion beam into isochronous spatial focus being exactly the distance between P3 and the detector in this case. Only half of the field free region is taken up on its outward trip to the right hand half of the parabolic potential well. When this half is switched OFF the ions of interest fly the remaining required field free region to be brought into isochronous spatial focus. It is the combination of a geometry that allows a portion of field free region along with a parabolic potential well allowing simple harmonic motion that makes such a multipass instrument possible. Without such a field free region there would be nowhere to position the detector without distortion of the electric fields.

If a higher degree of spatial focussing is required then the pulsed parabolic potential well may be contained in a field free region of a reflectron Time of Flight mass analyser. This further embodiment will now be described with reference to FIGS. 9A-9F.

Figure 9C:
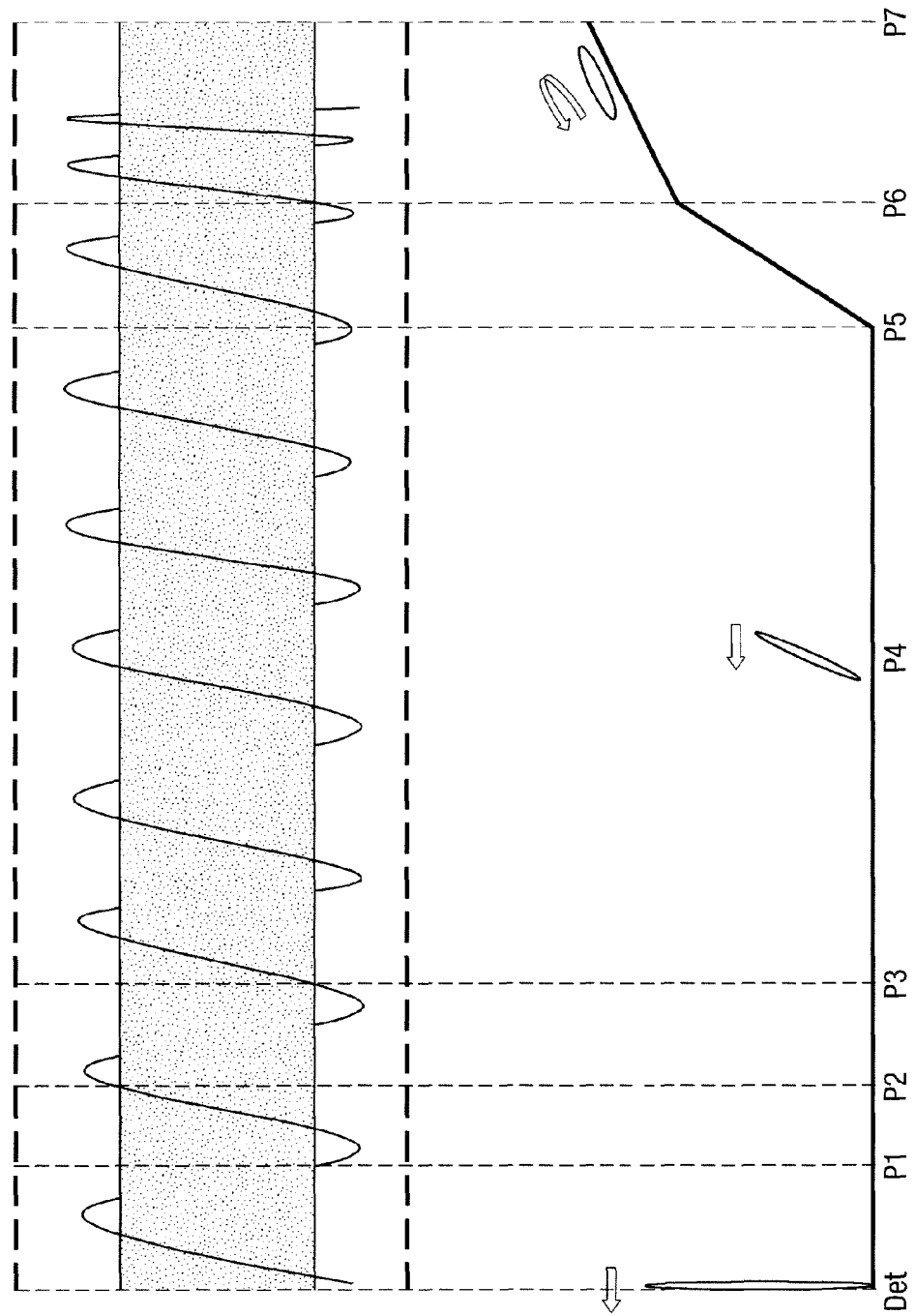
FIG. 9C shows ions being detected by an ion detector located at the exit of a field free region.
Figure 9D:
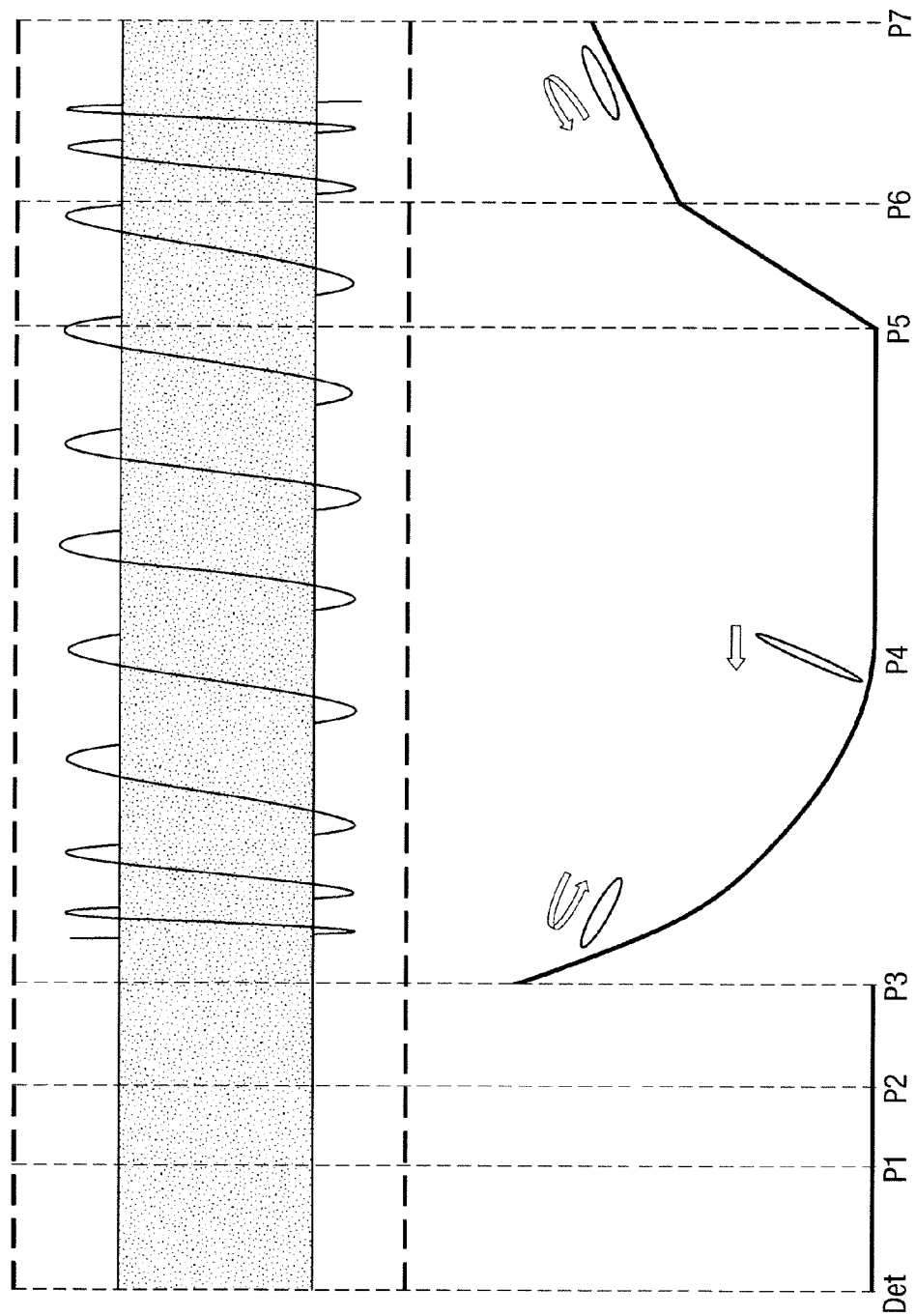
FIG. 9D shows an embodiment wherein ions experience a parabolic potential.

The principle of operation according to this embodiment is similar to that described above with reference to FIGS. 8A-8D, but also includes a single pass mode as shown in FIGS. 9A-9C which does not include the pulsing of the parabolic potential well. Such a mode of operation is particularly useful when faster acquisition at lower resolution is required. The higher degree of spatial focussing enables the very highest possible resolution to be achieved for the lowest number of passes of the potential well.

As will be understood by those skilled in the art, the mass range of the Time of Flight mass analyser will reduce with the number of round trips made of the harmonic potential well. If the analyser is traversed a number of times N then the available mass range reduces with this value in the relation:

$$m_{max}/m_{min} = (N/(N-1))^2 \qquad (1)$$

This could be seen as a disadvantage but the reduced mass range may be exploited by optimising the phase space conditions of the beam entering the analyser prior to acceleration. Generally ion beams are conditioned by a combination of RF focussing elements such as ring stacks, quadrupoles or higher order multipoles and electrostatic elements such as lenses and grids. Optimisation of initial conditions involves confining the beam closely to the optic axis. Most often the beam is confined tightly to the optic axis by using an RF only quadrupole but this device has a strong mass dependence in its focussing action. This means that while ions of a certain mass may be effectively squeezed to the optic axis, ions of higher mass are less strongly confined and ions of lower mass may be unstable in the device or pick up excessive energy from the RF field.

Accordingly, the transmission of a limited mass range to the analyser determined by the number of round trips enables optimisation of phase space characteristics for the masses contained within the reduced mass range for best possible instrument resolution.

WO 2011/154731 (Micromass) describes how an ion beam may be expanded to optimise phase space conditions in a conventional two stage Wiley McLaren instrument. WO 2011/154731 discloses how the limiting turnaround time aberration in a properly expanded beam scales with the acceleration potential difference seen by the beam rather than the electric field in that region.

Figure 10:
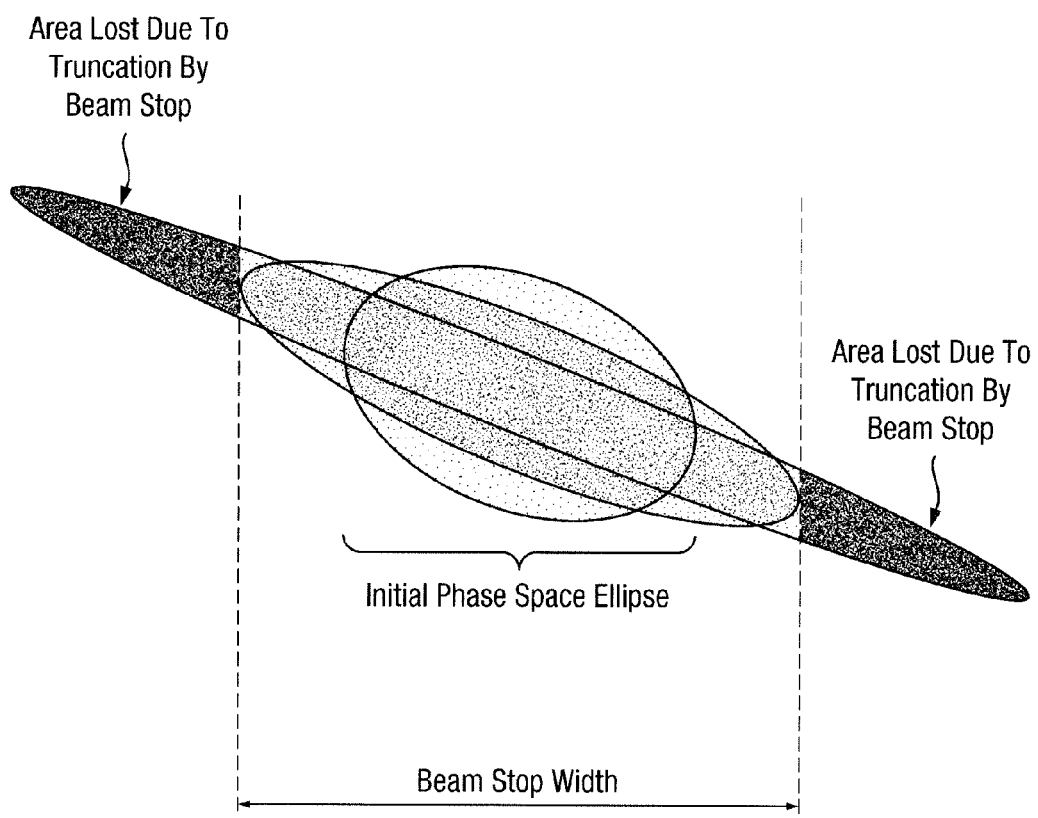
FIG. 10 shows evolution of phase space in pre push state with beam stop.

The preferred embodiment of the present invention allows for perfect aberration free beam expansion by allowing a packet of ions which has been injected into the analyser to rotate around the central electrode for as long as desired before orthogonal acceleration. The analyser is entirely field free in the axial direction before the acceleration pulse is applied. This allows free expansion due to the ions initial velocity. The process is essentially similar to having a variable flight distance from the transfer optics to the Time of Flight mass analyser. As the ions rotate and expand the phase space ellipse becomes more elongated and the beam picks up more of the acceleration potential when it is applied. So long as the analyser has a good enough spatial focussing characteristic then resolution will improve as the beam is allowed to expand. By prudent placing of an aperture plate (or beam stop) within the Time of Flight mass analyser acceleration region the maximum size that the beam can axially expand to may be limited to the spatial focussing characteristic of the analyser. If once the position of the beam stop is reached the ions are allowed to rotate further prior to acceleration, the phase space will take the form of a truncated ellipse getting thinner in the velocity direction the longer the rotation takes. This is illustrated in FIG. 10.

By varying the delay time greater resolutions may be reached at the expense of some ion losses. This may be thought of as analogous to the technique of delayed extraction in MALDI instruments whereby the ions are allowed to leave the target plate and adopt positions correlated with their initial velocity in the ion source prior to extraction into the analyser. The correlation of ion velocity and position is very high due to the desorption event being defined by a plane. The delayed extraction according to embodiments of the present invention does not have such complete position/velocity correlation but nevertheless high degrees of ion focussing can be achieved and can be further optimised for the mass range of interest being injected into the analyser i.e. the delay time may be set to allow the central mass in the injected range to just reach the position of the beam stop (i.e. fill to the level before spatial focussing degrades the resolution) before extraction takes place.

U.S. Pat. No. 546,495 (Cornish) discloses using a curved field reflectron to bring ions of wide kinetic energy difference created by post source decay ("PSD") in MALDI Time of Flight mass analyser instruments. According to an embodiment of the present invention such an arrangement may be utilised to give a first acceleration stage with good spatial focussing and the field free region necessary for suitable positioning of the ion detector.

As mentioned above, further embodiments of the present invention are contemplated wherein no grid electrodes are utilised. The radial confinement afforded by the stable orbit means that the ions adopt a narrow range of radial positions. This means that it is possible to make the entire system gridless and still maintain good spatial focussing while avoiding the disturbance in the axial electric fields and ion losses that these elements introduce. Gridless Time of Flight mass analysers without the radial stability of the present invention suffer from the defocusing effect of the electric fields caused by overfilling of the ion optical elements ultimately limiting device sensitivity and resolution.

Figure 11:
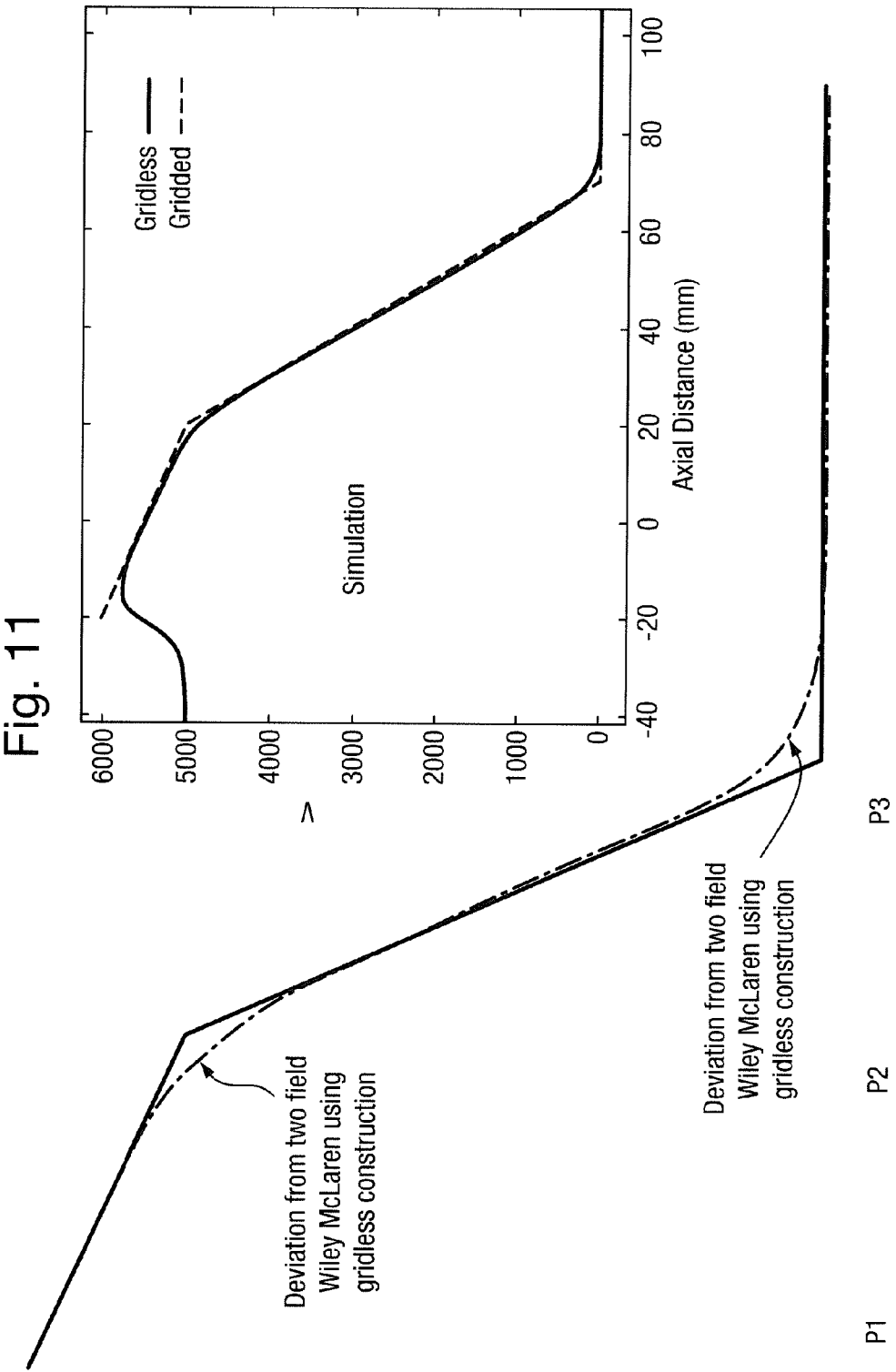
FIG. 11 shows a further embodiment of the present invention comprising a gridless geometry with pulsed voltages shown as dotted lines.

An example of a gridless electrode arrangement according to an embodiment of the present invention is shown in FIG. 11. In this case the electric potentials to be pulsed are shown as dotted lines but the order and nature of their pulsing and the phase space evolution is similar to that described with reference to FIGS. 8A-8D. Elimination of grid electrodes has a further advantage in that is simplifies the method of construction as the device may consist of two concentric segmented cylinders assembled independently rather than having common mechanical parts (e.g. grid electrodes) in contact with both outer and inner assemblies within the internal space between the two.

Modelling of a coaxial Time of Flight mass analyser according to an embodiment of the present invention was performed. Results from an analytic system were compared with resulting from a SIMION® simulation of a coaxial Time of Flight mass analyser geometry according to the preferred embodiment.

Figure 12:
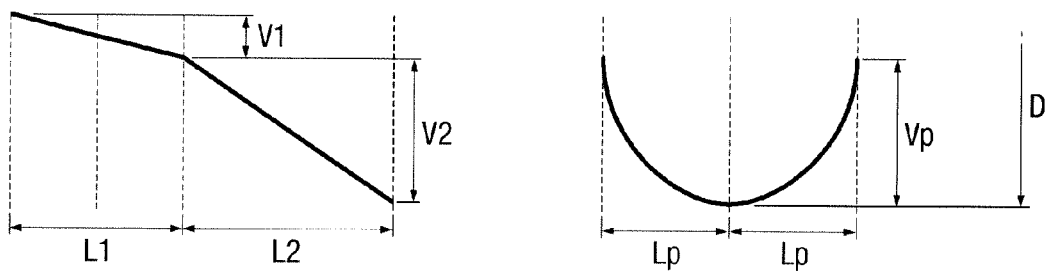
FIG. 12 shows a schematic of the geometry of a Time of Flight mass analyser which was modelled.

FIG. 12 shows the Time of Flight mass analyser geometry used for the modelling where the mean ion start plane is at the centre of the pusher region of length L1=40 mm. The voltage V1 equals 1000 V.

The acceleration region L2 was set at 50 mm and voltage V2 was set at 5000 V. The various regions are bounded by grid electrodes while the parabolic regions are not grid bounded. The distance Lp was modelled as being 99 mm and Vp was set at 10,000 V. The left hand parabola (LHP) is ramped up after ions are in the right hand parabola (RHP). The RHP is ramped down while the ions are in the LHP after the desired number of passes have occurred.

In the python model the total field free distance is a variable that can be solved while in the SIMION® simulation the ions are recorded at a fixed detector plane distance. These ions can then be imported into the python model and can be solved for a variable field free region, hence both approaches can be brought into focus.

Figure 13:
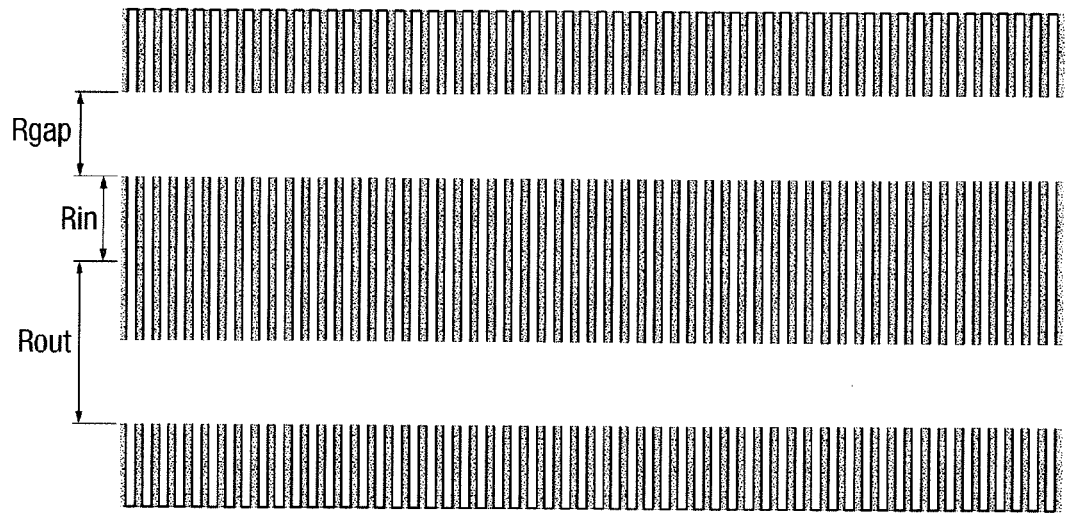
FIG. 13 shows a view of the co-axial geometry of a Time of Flight mass analyser which was modelled.

FIG. 13 shows the co-axial geometry used in the SIMION® modelling. The radius of the inner cylinder Rin was set at 10 mm and the outer cylinder radius Rout was set at 20 mm. Accordingly, Rgap equals 10 mm.

The axial electrode segments were arranged to be 1 mm wide with 1 mm gaps therebetween. Grid electrodes were modelled as being located between segments and voltages were modelled as being applied to give linear voltage drops across the first two regions and quadratic potentials in the parabolic regions.

A potential difference was applied between the inner and the outer cylinders to give radial confinement. In the results presented +650 V was applied to the outer cylinder and the inner cylinder is at the same potential as the grids.

For singly charged ions having a mass to charge ratio of 500 with 500 eV of radial KE and +650 V being applied to the outer cylinder gives good radial confinement. Significant radial KE is required to retain confinement within the parabolic regions which give radial divergence.

Figure 14:
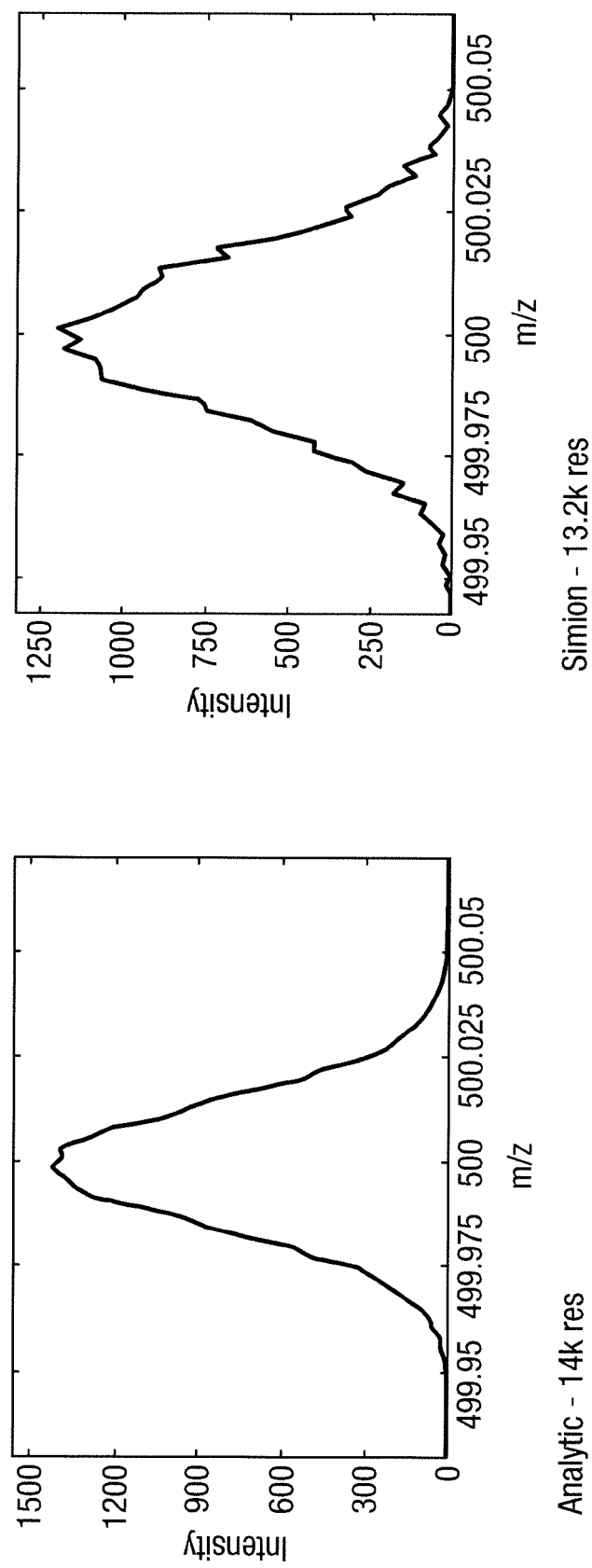
FIG. 14 shows a comparison of ion peaks due to an analytic system and a Time of Flight mass analyser according to an embodiment of the present invention.

For the first system the initial ion conditions were 1 mm position delta (+/−0.5 mm), Gaussian velocity spread with a 5 m/s standard deviation, no initial ion drift, 8 passes through the parabolic regions (1 pass is into then back out of a single parabola) and 10 kV on the parabolas. The results are shown in FIG. 14.

The total FFR is 1203 mm for the analytic system with 70.712 μs drift time. For the Time of Flight mass analyser according to the preferred embodiment the FFR is 1619 mm with a 79.617 μs drift time. The resolution performance of the Time of Flight mass analyser according to an embodiment of the present invention is comparable with the analytic system.

If the initial phase space is set smaller and more passes through the parabolas are allowed then the resolution according to the preferred embodiment is further improved. For this system the initial ion conditions were 0.2 mm position delta (+/−0.1 mm), Gaussian velocity spread with a 1 m/s standard deviation, no initial ion drift, 32 passes through the parabolic regions (1 pass is into then back out of a single parabola) and 10 kV on the parabolas.

The analytic system had a FFR of 1203 mm whereas the FFR according to the preferred system was 1630 mm. The resolution of the analytic system was 189,000 compared with 170,000 resolution for system according to the preferred embodiment.

It will be appreciated that a Time of Flight mass analyser having a potential resolution of 170,000 represents a very significant advance in performance compared with current state of the art commercial Time of Flight mass analysers.

Figure 15:
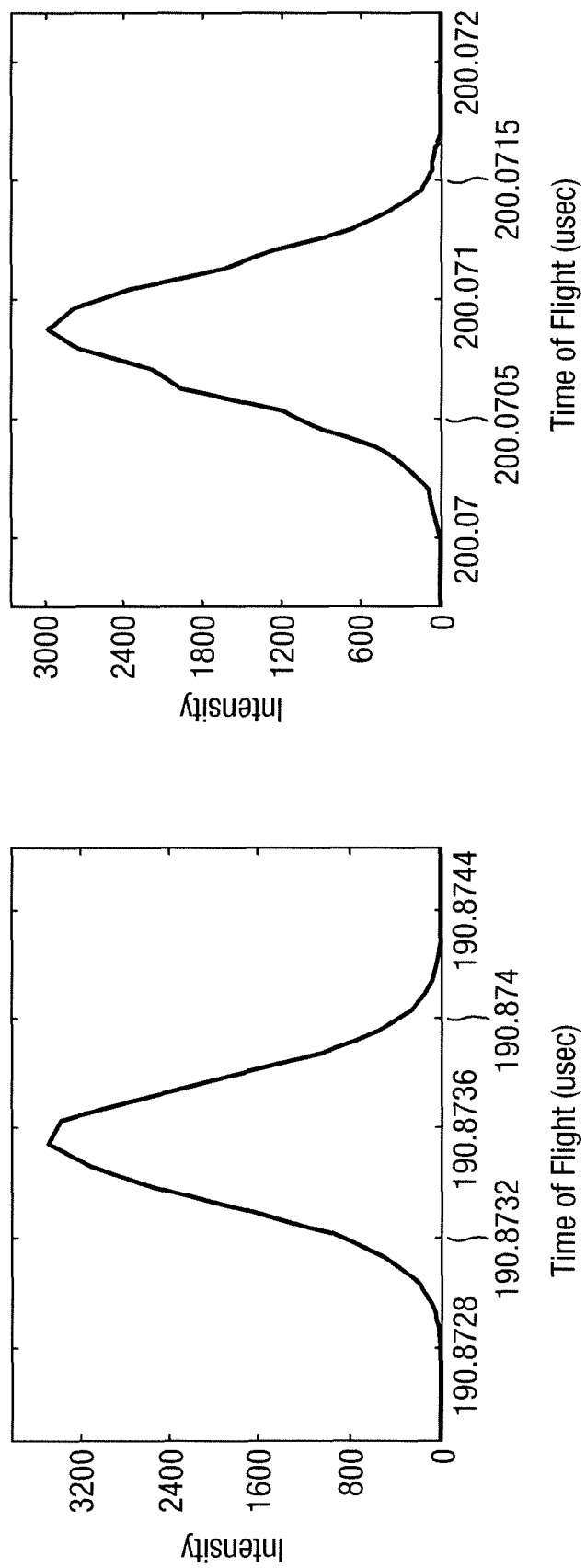
FIG. 15 shows a comparison of time of flight peaks due to an analytic system and a Time of Flight mass analyser according to an embodiment of the present invention.

Although the analytic and SIMION® systems are not in exact agreement it is apparent that the preferred embodiment is able to achieve about 90% of the analytic resolution. The flight time for the analytic system was 191 μs whereas the flight time for the preferred embodiment was 200 μs as shown in FIG. 15. In both cases the flight time is not excessively long (12 GHz TDC detector).

Unique Path Through Multipass Co-Axial Cylinder TOF

It is a distinct disadvantage of known multipass Time of Flight mass spectrometers that the mass range reduces as the number of passes through the analyser increases. This is because it is impossible to distinguish a faster lower mass ion from a slower higher mass ion which may have made a lower number of analyser passes. Consequently, only a small subset of the mass range to be analysed may be injected into the spectrometer so as to avoid aliasing at the chosen number of roundtrips of the analyser.

An important feature of a preferred embodiment of the present invention is that a unique path is provided for all ions of all masses so that the entire mass range may be covered in a single acquisition cycle. The present invention therefore represent a significant improvement in the art.

Ions are preferably injected into a segmented coaxial cylinder Time of Flight mass spectrometer using a switched sector with no axial field. The ions are preferably injected such that they describe circular trajectories in the cylindrical pusher region of the spectrometer. The ions are allowed to rotate around the central electrode set and expand to fill the pusher so that they see a large voltage drop when the extraction field is subsequently activated to minimise the turnaround time.

The extraction field is preferably activated to give an axial and radial impetus to the circularly rotating ion beam. The axial field is preferably created using a quadratic potential function so that the ions preferably exhibit substantially simple harmonic motion in the z-direction (the direction of Time of Flight analysis). The radial field is also pulsed at the same time such that the ions no longer describe perfect circular orbits but rather they begin to describe eccentric orbits which allow a variation in the radial position as they traverse the analyser. The ions preferably exhibit radial oscillations which are independent in frequency to those in the axial direction. In other embodiments the ions may describe unstable trajectories sending them in an inward or outward direction. In either case it is desired that the ions describe a unique path in the analyser describing a number of oscillations in the z direction before they strike an ion detector which is preferably placed inside the analyser perpendicular to the z axis and at a position preferably corresponding to the isochronous plane.

It is an advantage of the present invention that the ions are free to expand in the angular φ coordinate as the ion detector may take the form of an annulus so capturing all ions regardless of φ i.e. no constraint or control of the ions is preferably required in the φ direction.

The segmented construction of the device and the inherent decoupling of the applied axial and radial field components allows for independent control of radial and axial motion which is not possible using cylindrical electrodes of solid construction that can only satisfy the boundary conditions for a fixed ratio of radial to axial field strength.

A particularly preferred embodiment of the present invention is shown in FIG. 16A. Ions are injected between an outer segmented electrode set O1 and an inner segmented injection electrode set I1 where they are allowed to rotate and axially expand by virtue of their thermal velocity (from the ion source).

Figure 16B:
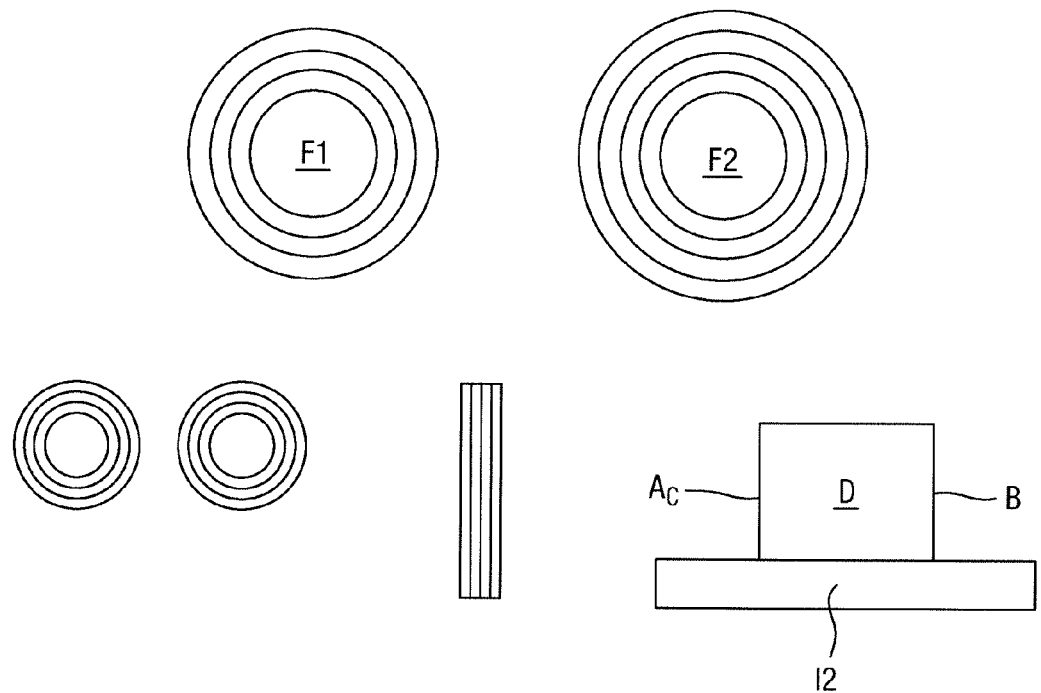
FIG. 16B shows conductive rings on a PCB substrate and FIG. 16C shows a microchannel plate ion detector which enables a radial potential to be maintained across the surface of the ion detector.
Figure 16C:
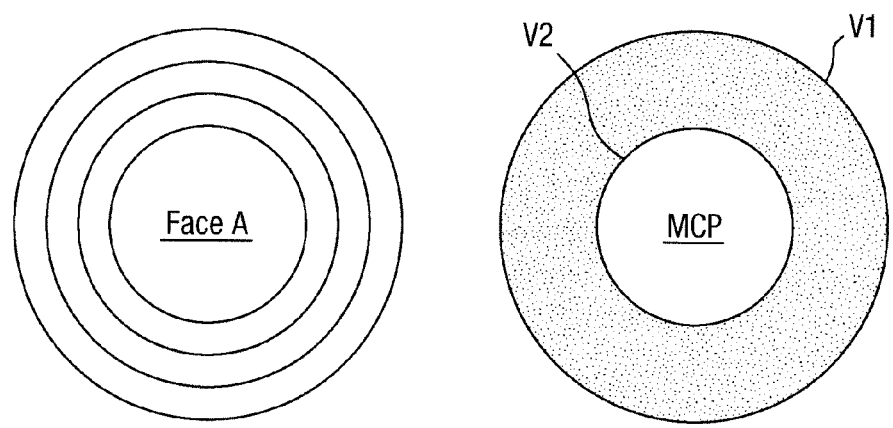

Pulsed radial and axial fields are then preferably applied and move the ion beam into the central portion of the analyser where they oscillate with radial amplitude δR and axial amplitude δz. The injection segment of the analyser may be narrower than that of the central part so as to minimise aberrations on entry to the switched sector region. According to an embodiment the axial field is preferably raised further when the ions first enter the main body of the device so as to prevent the ions from striking the narrower injection region due to radial oscillation imparted by the pulsed component of the radial field. This gives a small mass dependence in Time of Flight trajectory but does not change the position of the isochronous plane P1. In order to control the fringe fields at the ends of the device and at the position of the ion detector some optical components may be incorporated that closely follow the boundary conditions of the desired analytical field F1, F2 and the surfaces of the ion detector D. These may take the form of conductive rings on PCB substrates to which are applied the correct voltage (FIG. 16B). In the case of a microchannel plate detector its resistive nature may be utilised and the boundary conditions may be satisfied by applying radial voltages V1 and V2 between its inner and outer regions as shown in FIG. 16C.

According to the preferred embodiment the ions preferably miss the ion detector for a predetermined number of passes by controlling the frequency, amplitude and phasing of the radial oscillations.

Derivation of Equations of Motion

The equations of motion may be derived using the Lagrangian formulation. The Lagrangian is the difference between the kinetic energy and the potential energy. In cylindrical polar coordinates with a time-independent and cylindrically symmetric potential this is:

$$L = T - V = \tfrac{1}{2}m[(r\dot\phi)^2 + \dot r^2 + \dot z^2] - qU(r,z) \qquad (2)$$

The three Euler-Lagrange equations are:

$$\frac{\partial}{\partial t}\frac{\partial L}{\partial \dot q_i} - \frac{\partial L}{\partial q_i} = 0 \qquad (3)$$

one for each of the three $q_i$ cylindrical coordinates r, φ and z. For the class of potentials that are of interest:

$$m(\ddot r - r\dot\phi^2) = -q\frac{\partial U(r,z)}{\partial r} \qquad (4)$$

$$m\ddot z = -q\frac{\partial U(r,z)}{\partial r} \qquad (5)$$

$$\frac{\partial}{\partial t}(mr^2\dot\phi) = 0 \qquad (6)$$

Some general conclusions can be drawn. Firstly, the motion in the z direction is decoupled from orbital motion in the (r, φ) plane when the potential can be written in the form:

$$U(r,z) = U_r(r) + U_z(z) \qquad (7)$$

Second, Eqn. 6, which expresses conservation of angular momentum $L_z$ for motion around the z axis can be rewritten as:

$$\dot\phi(t) = \frac{L_z}{mr^2(t)} \qquad (8)$$

which implies that unless φ is constant ($L_z$=0 corresponds to pure radial motion), or the radius is constant (pure circular motion), then motion in r and φ is coupled. When Eqn. 7 is satisfied, the problem reduces to the differential equations for the radial variable and variable which are respectively:

$$m\left(\ddot r - \frac{L_z^2}{m^2 r^3}\right) = -q\frac{\partial U_r}{\partial r} \qquad (9)$$

$$m\ddot z = -q\frac{\partial U_z}{\partial r} \qquad (10)$$

and given r(t), φ(t) can be obtained by integrating Eqn. 8.

The radial equation of motion Eqn. 9 can be reformulated as follows:

$$m\ddot r = -q\frac{\partial \tilde U_r}{\partial r} \qquad (11)$$

where the effective radial potential includes a centrifugal term:

$$\tilde U_r(r) = U_r(r) + \frac{L_z^2}{2mqr^2} \qquad (12)$$

The energy $E_{r\phi}$ is conserved:

$$E_{r\phi} = \tfrac{1}{2}m\dot r^2 + q\tilde U_r(r) \qquad (13)$$

An initial condition that is of particular interest occurs when ions attain their initial velocity by acceleration through a potential drop ΔU. For simplicity, it is assumed that the injection radius is $R_0$ and the initial radial velocity r(0)=0. In this case the angular momentum satisfies:

$$L_z^2 = 2mqR_0^2\Delta U \qquad (14)$$

so that:

$$\tilde U_r(r) = U_r(r) + \frac{R_0^2 \Delta U}{r^2} \qquad (15)$$

which is explicitly independent of q and m. It will be noted that unusually for a potential, Ũ, changes with the initial conditions ($R_0$ and $\Delta U$ or, equivalently, the orbital angular momentum $L_z$). However, for fixed $U_r(r)$, the mapping:

$$R_0 \to R'_0, \Delta U \to \Delta U \frac{R_0^2}{R_0'^2} \quad (16)$$

leaves the angular momentum and the effective potential unchanged. Stable circular orbits may be obtained when it is possible to choose the quantity $R_0^2 \Delta U$ in such a way that $r=R_0$ is a minimum of the effective potential $\tilde{U}_r(r)$.

Orbital Differential Equation

A differential equation for the orbit $r(\phi)$ can also be obtained. First from Eqn. 8 the following can be obtained:

$$d\phi = \frac{L_z}{mr^2} dt \quad (17)$$

and thence:

$$\frac{d}{dt} = \frac{L_z}{mr^2} \frac{d}{d\phi} \quad (18)$$

which enables the time derivative to be eliminated in favour of a $\phi$ derivative:

$$m\ddot{r} = m\frac{d^2r}{dt^2} = \frac{L_z^2}{m} \frac{1}{r^2} \frac{d}{d\phi}\left(\frac{1}{r^2} \frac{dr}{d\phi}\right) = -2qR_0^2 \Delta U u^2 \frac{d^2u}{d\phi^2} \quad (19)$$

where Eqn. 14 has been used and introduced the new variable $u=1/r$. Noting that:

$$\frac{d}{dr} = -u^2 \frac{d}{du} \quad (20)$$

the equation of motion Eqn. 11 becomes a differential equation for the orbit:

$$\frac{d^2u}{d\phi^2} = \frac{-1}{2R_0^2 \Delta U} \frac{d\tilde{U}_r(1/u)}{du} \quad (21)$$

With initial conditions, if the effective potential $\tilde{U}_r$ is independent of $q$ and $m$ then the same will be true of $u(\phi)$ and therefore $r(\phi)$.

Time Dependence and Orbital Period

Ions are initially set up in a circular orbit. The times at which bounded orbits reach various radii are of interest. For central forces the orbit is symmetric about each of its turning points, and the first traversal from $r=R_{max}$ to $r=R_{min}$ (or vice-versa) enables relevant equations to be derived. Furthermore $t(r)$ is single value in this range.

Starting from the energy conservation Eqn. 13 then since the starting point is a circular orbit and a pulse in the field at $t=0$ then the initial conditions will be $r(0)=R_{max}$ and $\dot{r}(0)=0$. Alternatively, it is possible to start at $r=R_{min}$ but the conclusions would be essentially the same. The following equation can therefore be written:

$$q\tilde{U}_r(R_{max}) = \tfrac{1}{2}m\dot{r}^2 + q\tilde{U}_r(r) \quad (22)$$

which can be rearranged as:

$$\dot{r} = -\sqrt{\frac{2q}{m}(\tilde{U}_r(R_{max}) - \tilde{U}_r(r))} \quad (23)$$

where the negative square root is taken since it is known that $\dot{r}<0$ in the part of the trajectory that is relevant. This may be rewritten in the following form:

$$dt = -\sqrt{\frac{m}{2q}} \frac{dr}{\sqrt{(\tilde{U}_r(R_{max}) - \tilde{U}_r(r))}} \quad (24)$$

which can be integrated to give:

$$t(r) = \sqrt{\frac{m}{2q}} \int_r^{R_{max}} dr (\tilde{U}_r(R_{max}) - \tilde{U}_r(r))^{-1/2} \equiv \sqrt{\frac{m}{q}} \tau(r) \quad (25)$$

where for convenience $q$ and $m$ have been introduced and the independent function $\tau(r)$:

$$\tau(r) = \frac{1}{\sqrt{2}} \int_r^{R_{max}} dr [\tilde{U}_r(R_{max}) - \tilde{U}_r(r)]^{-1/2} \quad (26)$$

The period of the radial orbit is the time taken to reach $R_{min}$ and return to $R_{max}$ which is:

$$T_r = 2t(R_{min}) = 2\sqrt{\frac{m}{q}} \tau(R_{min}) \quad (27)$$

Unfortunately, for the class of potentials that are of interest, this integral cannot be performed analytically. However, numerical solutions may be obtained in a straightforward manner.

Decoupled Solutions of Laplace's Equation

It is desired to find the general solution of Laplace's equation with cylindrical symmetry and the constraint that the field at fixed radius $r$ is quadratic in the axial direction $z$.

Laplace's equation in cylindrical polar coordinates may be written as follows:

$$\nabla^2 U(r, \phi, z) = \left(\frac{1}{r}\frac{\partial}{\partial r} r \frac{\partial}{\partial r} + \frac{1}{r^2}\frac{\partial^2}{\partial \phi^2} + \frac{\partial^2}{\partial z^2}\right) U(r, \phi, z) = 0 \quad (28)$$

Since solutions with cylindrical symmetry are desired the angular dependence can be dropped to give (for all $\phi$):

$$\left[\frac{1}{r}\frac{\partial}{\partial r} r \frac{\partial}{\partial r} + \frac{\partial^2}{\partial z^2}\right] U(r, z) = 0 \quad (29)$$

A solution of the form is desired:

$$U(r,z) = a(r)z^2 + b(r) \quad (30)$$

which is quadratic in z for fixed r. Substituting this into Eqn. 29 gives:

$$z^2 \frac{1}{r}\frac{\partial}{\partial r} r \frac{\partial}{\partial r} a(r) + 2a(r) + \frac{1}{r}\frac{\partial}{\partial r} r \frac{\partial}{\partial r} b(r) = 0 \tag{31}$$

In order for this equation to be satisfied for all values of z the first term must vanish:

$$z^2 \frac{1}{r}\frac{\partial}{\partial r} r \frac{\partial}{\partial r} a(r) = 0 \tag{32}$$

which can be integrated directly to give:

$$a(r) = a_0 \ln(r/r_0) + \frac{k}{2} \tag{33}$$

wherein $r_0$ is an arbitrary constant with dimensions of length which is introduced to keep the argument of the logarithm explicitly dimensionless. Substituting back into Eqn. 31 yields:

$$\frac{\partial}{\partial r} r \frac{\partial}{\partial r} b(r) = -2a_0 r \ln(r/r_0) - kr \tag{34}$$

which can be integrated once more to give:

$$\frac{\partial}{\partial r} b(r) = a_0 r \left[\frac{1}{2} - \ln(r/r_0)\right] - \frac{k}{2}r + b_0/r \tag{35}$$

and again:

$$b(r) = \frac{a_0 r^2}{2}(1 - \ln(r/r_0)) - \frac{k}{4}r^2 + b_0 \ln(r/r_0) + b_1 \tag{36}$$

The general solution may be written:

$$U(r, z) = \tag{37}$$
$$\frac{k}{2}(z^2 - r^2/2) + b_0 \ln(r/r_0) + b_1 + a_0\left[z^2 \ln(r/r_0) + \frac{r^2}{2}(1 - \ln(r/r_0))\right]$$

Setting $a_0=0$ so that the axial motion is decoupled from motion in the r, φ plane, then the potential is:

$$U(r, z) = \frac{k}{2}(z^2 - r^2/2) + b_0 \ln(r/r_0) + b_1 \tag{38}$$

with a unique z-independent stationary point in the radial direction at:

$$R_m = \sqrt{\frac{2b_0}{k}} \tag{39}$$

which is a maximum for k>0. This field can approximated using a series of closely spaced (in z) pairs of coaxial annular electrodes of arbitrary outer and inner radius $R_1$ and $R_2$. The potentials that must be applied to the electrodes at axial position z are:

$$U_1(z) = \frac{k}{2}(z^2 - R_1^2/2) + b_0 \ln(R_1/r_0) + b_1 \tag{40}$$

$$U_2(z) = \frac{k}{2}(z^2 - R_2^2/2) + b_0 \ln(R_2/r_0) + b_1$$

There is no mathematical constraint on the k, $b_0$, $b_1$ or consequently $R_m$ that can be produced in this way. The equations of motion corresponding to the potential Eqn. 37 are:

$$(\ddot{r} - r\dot{\phi}^2) = \frac{q}{m}\left[\frac{k}{2}r - \frac{b_0}{r}\right] \tag{41}$$

$$\ddot{z} = -\frac{qk}{m}z \tag{42}$$

$$\frac{\partial}{\partial t}(r^2 \dot{\phi}) = 0. \tag{43}$$

Axial Motion

When k=0, Eqn. 42 describes simple harmonic motion in the z direction. The solution is well known. For an ion with initial position z(0) and z-velocity ż(0):

$$z(t) = z(0)\cos\omega_z t + \frac{\dot{z}(0)}{\omega_z}\sin\omega_z t \tag{44}$$

where the angular frequency $\omega_z = \sqrt{qk/m}$. The period is $T = 2\pi/\omega_z$.

Circular Orbits

To obtain circular orbits (ignoring axial motion) it is required that $\ddot{r}=\dot{r}=0$. From Eqn. 43 it may be inferred that $\ddot{\phi}=0$ which implies that these trajectories have constant angular velocity with, from Eqn. 41:

$$\dot{\phi}^2 = \frac{q}{m}\left[\frac{b_0}{R_0^2} - \frac{k}{2}\right] \tag{45}$$

for a circular orbit of radius $R_0$. This expression is valid as long as $R<R_m$.

The General Orbit

To treat more general orbits the effective radial potential Eqn. 15 for the particular potential Eqn. 38 may be considered. By choosing $\dot{r}(0)=0$ the trajectory may be started at a radial turning point or stationary point. Ignoring irrelevant constant (or purely z dependent) terms:

$$\tilde{U}_r(r) = -\frac{k}{4}r^2 + b_0 \ln(r/r_0) + \frac{R_0^2 \Delta U}{r^2} \tag{46}$$

$$\frac{\partial \tilde{U}_r}{\partial r} = -\frac{k}{2}r + \frac{b_0}{r} - 2\frac{R_0^2 \Delta U}{r^3} \tag{47}$$

and therefore stationary points at $R_s$ satisfying:

$$-\frac{k}{2}R_s^4 + b_0 R_s^2 - 2R_0^2 \Delta U = 0. \tag{48}$$

or $$R_{s\pm}^2 \equiv \frac{b_0}{k}\left(1 \pm \sqrt{1 - \frac{4kR_0^2 \Delta U}{b_0^2}}\right) \tag{49}$$

which has two distinct solutions as long as:

$$b_0 > 2\sqrt{k\Delta U} R_0 \quad (50)$$

taking $k$, $b_0$, $\Delta U > 0$. The limiting behaviour of the effective potential Eqn. 46 is:

$$\lim_{r \to 0} \tilde{U}_r = \frac{R_0^2}{r^2} \Delta U \quad (51)$$

$$\lim_{r \to \infty} \tilde{U}_r = -\frac{k}{4} r^2$$

which is large positive for small r and large negative for large r so that the stationary points $R_{S-}$ and $R_{S+}$ defined by Eqn. 49 must be a minimum and maximum respectively. Consequently, the condition Eqn. 50 is necessary for the existence of bounded orbits which must also satisfy $r < R_{S+}$. The radius at perigree and apogee of bounded orbits may be denoted as $R_{min}$ and $R_{max}$ respectively. It is apparent that:

$$\tilde{U}_r(R_{min}) = \tilde{U}_r(R_{max}) \text{ and } R_{max} = R_0 \quad (52)$$

The nature of the trajectory with starting point $r=R_0$ is partly determined by the sign of the gradient of the effective potential Eqn. 47 at $r=R_0$. In particular, if the gradient (times $R_0$):

$$R_0 \tilde{U}'_r(r)\rho\big|_{r=R_o} = b_0 - 2\Delta U - \frac{k}{2} R_0^2 \quad (53)$$

is positive, the starting point is a radial maximum and the trajectory must be bounded. If the gradient is negative, then the starting point is a radial minimum and the orbit is bounded if (and only if) $R_O \leq R_{S+}$ and $\tilde{U}_r(R_O) \leq \tilde{U}_r(R_{S+})$. If the gradient is zero then the conditions for a circular orbit are satisfied (stable if $R_O = R_{S-}$ and unstable if $R_O = R_{S+}$).

Figure 17:
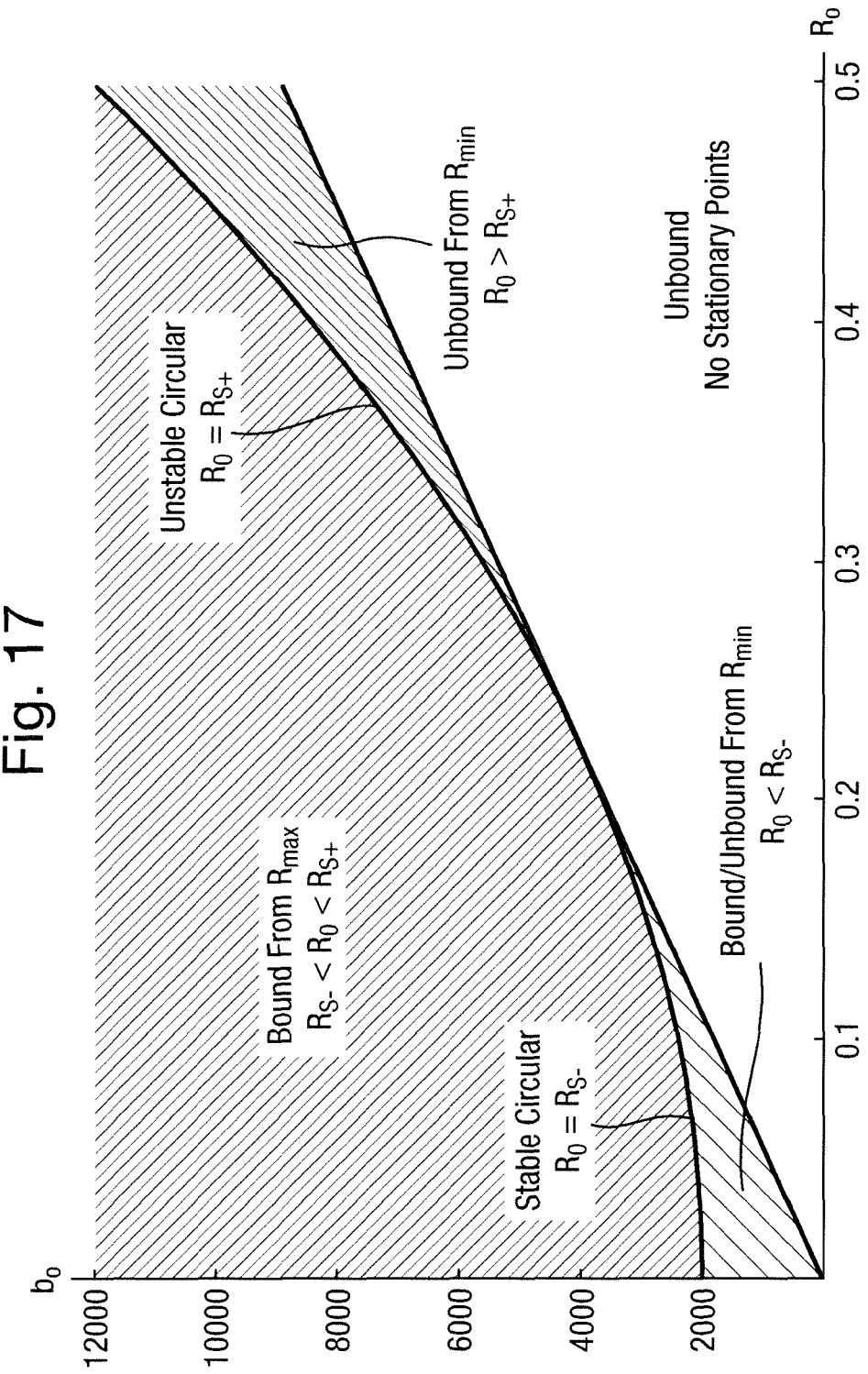
FIG. 17 shows trajectory classifications.

FIG. 17 shows the trajectories produced at points in the $(R_0, b_0)$ plane for fixed k and $\Delta U$. In the regions above the straight line $b_0 > 2\sqrt{k\Delta U} R_0$ the potential has two stationary points (a minimum and a maximum). In the region above the curved line $$b_0 > 2\Delta U + \frac{k}{2} R_0^2$$

the trajectory is bounded and starts at a radial maximum. The straight and curved lines meet at the point:

$$R_0 = 2\sqrt{\frac{\Delta U}{k}}, \quad (54)$$

$$b_0 = 4\Delta U$$

which corresponds to an unstable circular trajectory at an inflection point of the effective potential. The boundary between bound and unbound trajectories in the region below $R_O = R_{S-}$ is not shown on this plot. FIG. 17 shows trajectory classification for $k=8\times10^4$ Vm$^{-2}$ and $\Delta U=1000$ V. Above the straight line the effective potential has a minimum. Above the curved line the starting point is the radial maximum of a bound trajectory.

Figure 18:
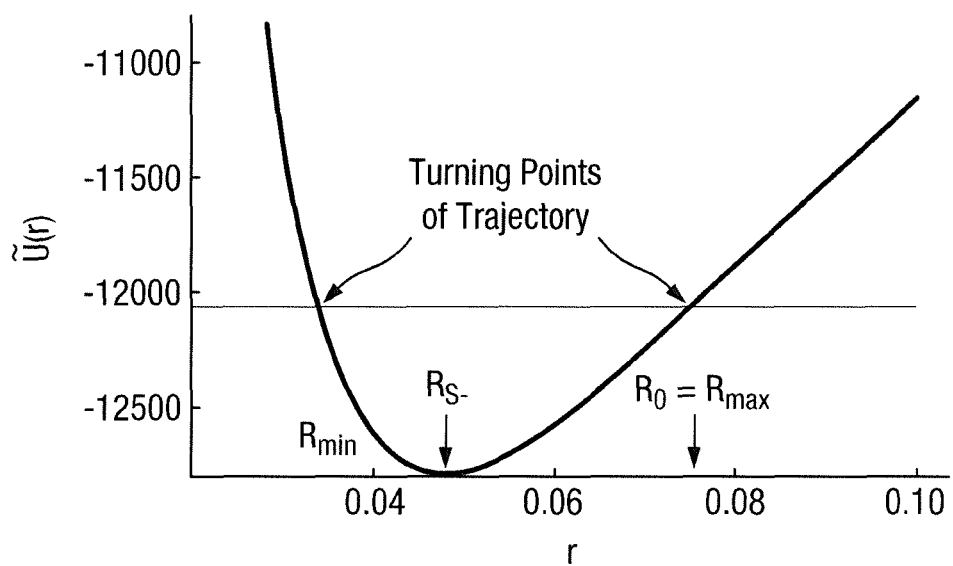
FIG. 18 shows an effective potential.

An example of an effective potential corresponding to a bound trajectory is shown in FIG. 18 with parameters $k=8\times10^4$ Vm$^{-2}$, $R_0=R_{max}=0.075$ m, $b_0=5000$ V and $\Delta U=1000$ V. The stationary points of the potential are at $R_{S-}=0.048$ m and $R_{S+}=0.350$ m (off scale). $R_{min}=0.034$ m. Starting at $r=R_0=R_{max}$ ions oscillate between $R_{min}$ and $R_{max}$.

Figure 19:
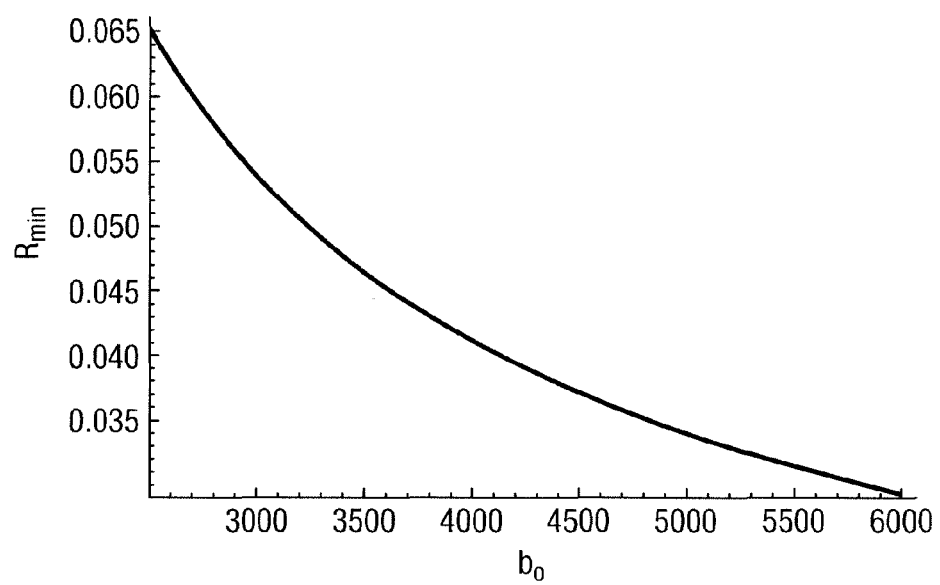
FIG. 19 shows the inner limit of an orbit.

FIG. 19 shows $R_{min}$ as a function of $b_0$ for the orbit corresponding to $k=8\times10^4$ Vm$^{-2}$ with $\Delta U=1000$ V and $R_0=0.075$ m. As $b_0$ increases (and with it the attractive part of the potential), $R_{min}$ decreases. It will be noted that the trajectories towards the right of this plot are highly eccentric.

Three Dimensional Trajectories

It is desired to find a set of trajectories which oscillate back and forth axially through the mass spectrometer, missing the ion detector for a predetermined number of passes $N-1 \geq 0$ and hit the ion detector on the final pass N. Considering the axial equation of motion Eqn. 44 with the added assumption that the ions start with no axial velocity i.e. $z(0)=0$. For brevity we shall also write $Z_0 = z(0)$.

$$z(t) = Z_0 \cos \omega_z t \quad (55)$$

This orbit passes the ion detector at times:

$$t_n = \frac{(2n-1)\pi}{2\omega_z}, n = 1, 2 \ldots \quad (56)$$

It is assumed for simplicity that the axial extent of the ion detector $W_d$ is small compared with the axial extent of the orbit i.e. $W_d \ll 2Z_0$. As ions pass the ion detector the ions have velocity $\dot{z} = \pm Z_0 \omega_z$ so the time taken to pass the ion detector is approximately:

$$\Delta T_d = \frac{W_d}{Z_0 \omega_z} = \frac{W_d}{Z_0 \sqrt{k}} \sqrt{\frac{m}{q}} \quad (57)$$

It is desired to find radial trajectories that satisfy $r(t) > H_d$ for $|t - t_n| < \Delta T_d/2$ when $n < N$ and $r(t) < H_d$ for $t = t_N$. It is desired to know the times at which the radial orbit reaches the critical radius $r=H_d$.

Ignoring initially the finite axial extent of the ion detector, it is noted that $R_{min}$ is achieved at odd multiples of one half of the radial period, while $z=0$ occurs at odd multiples of one quarter of the axial period. Assuming that $R_{min} < H_d$, ions are guaranteed to hit the ion detector when $r=R_{min}$ and $z=0$ simultaneously. This occurs for all pairs of positive integers j, n satisfying:

$$(2j-1)\frac{T_r}{2} = (2n-1)\frac{T_z}{4} \quad (58)$$

which may also be written:

$$\frac{2j-1}{2n-1} = \frac{1}{2}\frac{T_z}{T_r} \quad (59)$$

From Eqn. 27 the condition is therefore:

$$\frac{2j-1}{2n-1} = \frac{\pi}{2}\frac{1}{\sqrt{k} \, r(R_{min})} \quad (60)$$

which is independent of q and m as it must be, and $\tau(R_{min})$ is the integral Eqn. 26:

$$\tau(R_{min}) = \frac{1}{\sqrt{2}} \int_{R_{min}}^{R_{max}} dr \left[ \tilde{U}_r(R_{max}) - \tilde{U}_r(r) \right]^{-1/2} \quad (61)$$

FIG. 18 shows the effective potential with parameters $k=8\times10^4$ Vm$^{-2}$, $R_{11}=R_{max}=0.075$ m, $b_o=5000$ V and $\Delta U=1000$ V. The stationary points of the potential are at $R_{S-}=0.048$ m and $R_{S+}=0.350$ m (off scale). $R_{min}=0.034$ m.

To fulfill the condition that the detector is missed N−1 times for fixed k and $\Delta U$ a point must be chosen in $(b_0, R_0)$ space near which Eqn. 60 is satisfied for n=N but away from points at which the condition is met for 1<n<N.

Figure 20:
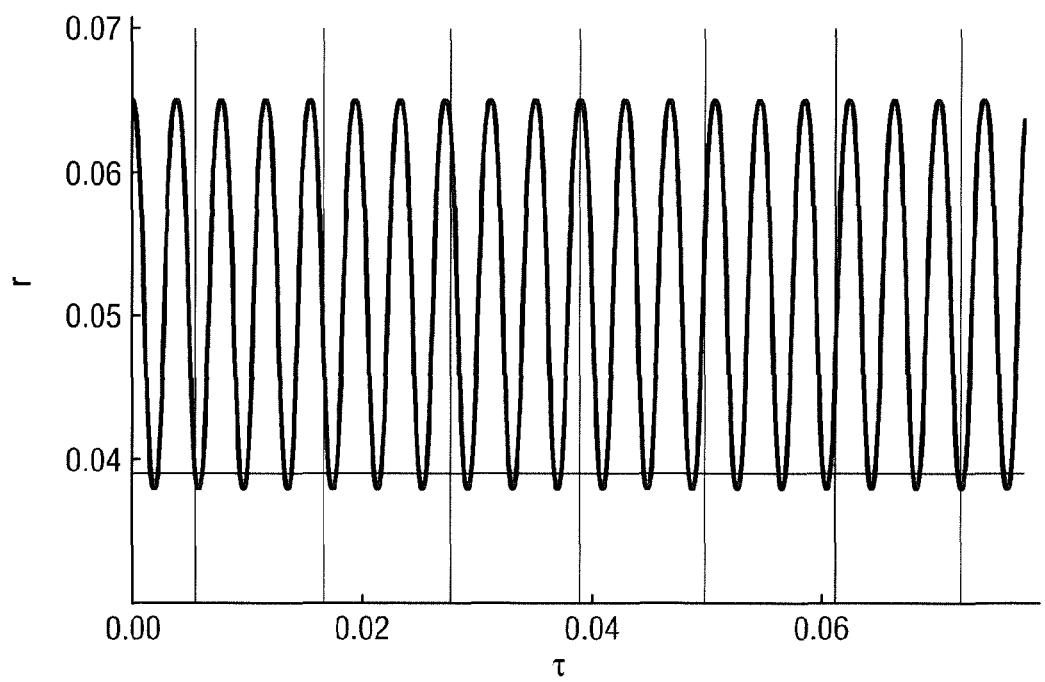
FIG. 20 shows radial motion as a function of T=t.

FIGS. 19 and 20 illustrate the trajectory corresponding to N=7, $j_{max}=19$ with an injection radius of r=0.065 m which passes the ion detector axially six times finally hitting on the seventh pass. FIG. 19 shows the inner limit of orbit for $k=8\times10^4$ Vm$^{-2}$, $\Delta U=1000$ V and $R_0=0.075$ m.

FIG. 20 shows radial motion as a function of $\tau=t\sqrt{q/m}$ for $k=8\times10^4$ Vm$^{-2}$, $\Delta U=1000$ V, $b_0=3700$ V and $R_0=0.065$ m. The horizontal line at r=0.039 m represents a possible detector surface. Ions pass the ion detector axially six times, finally hitting on the seventh pass after 18.5 radial cycles. The vertical lines correspond to values of T for which ions pass through the plane z=0. The $\Delta\tau$ to pass a detector with width $W_d=0.01$ m is invisible on the scale of this plot.

Figure 21:
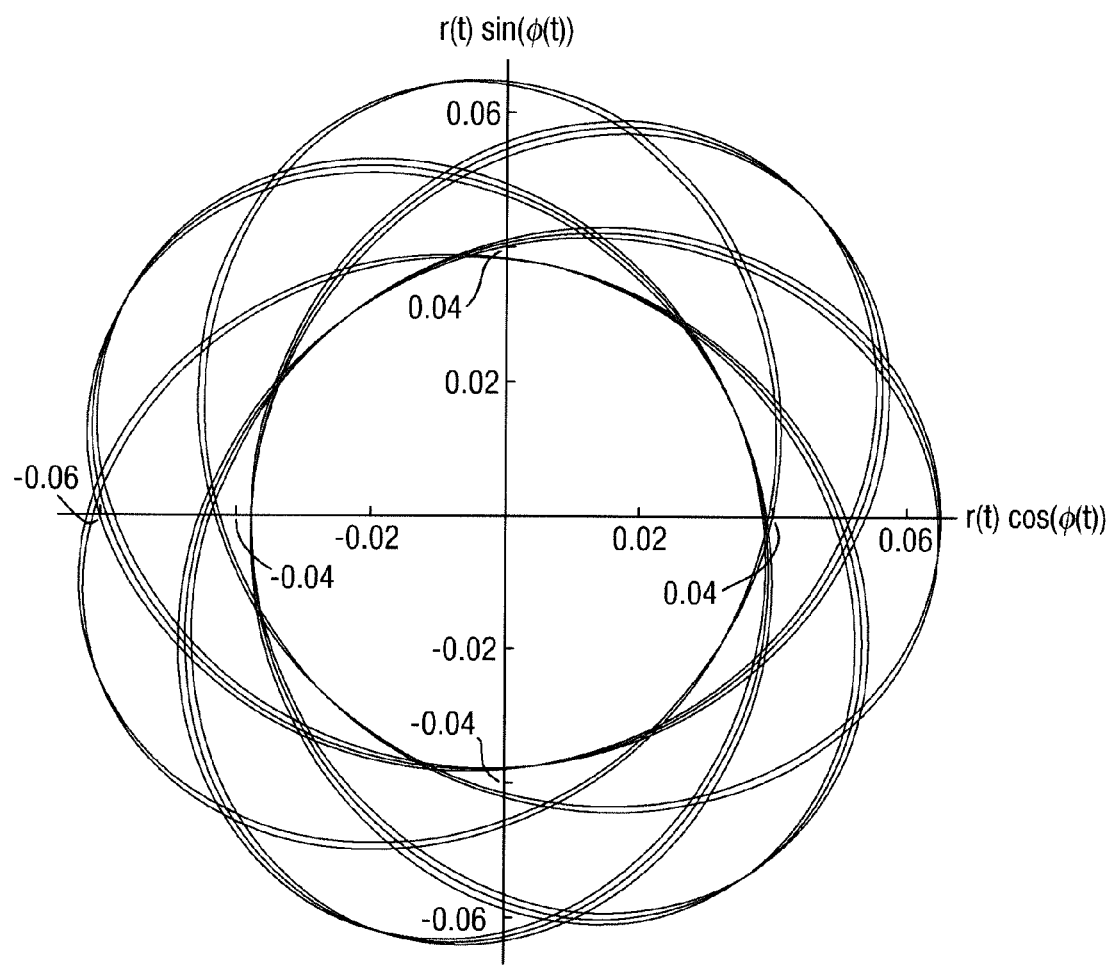
FIG. 21 shows orbital motion according to an embodiment.

FIG. 21 shows orbital motion for $k=8\times10^4$ Vm$^{-2}$, $\Delta U=1000$ V, $b_0=3700$ V and $R_0=0.065$ m.

According to an alternative embodiment the ion trajectory may start near an inflection point of effective radial potential and allow ions to spiral outwards to an annular detector.

According to another embodiment a radially bound trajectory may start at $R_{min}$ rather than $R_{max}$. In this case the injection radius would be lower than the outer detector radius.

Method of Ion Injection into Co-Axial Cylinder TOF

A less preferred method of injecting ions into the spectrometer so that they achieve a stable trajectory has been shown and described above with reference to FIG. 5. According to this less preferred embodiment stable trajectories may be achieved by reducing the voltage on the inner electrode with respect to the outer electrode as the ions enter the device. This approach requires a packet of ions of limited temporal distribution to be pulsed into the device. Ions injected in this way adopt a range of radial positions that have a slight mass dependency. This is not ideal since it is required that all ions experience the same overall fields in the axial direction as they traverse the Time of Flight mass analyser in order to achieve the highest possible resolution.

If ions are simply injected into a pair of coaxial cylinders through a small hole without scanning the internal field then no stable trajectories are achieved and the injected ions will always describe a trajectory that ends up outside the space between the concentric cylinders. Two examples of such trajectories are shown in FIGS. 22A and 22B.

Figure 22B:
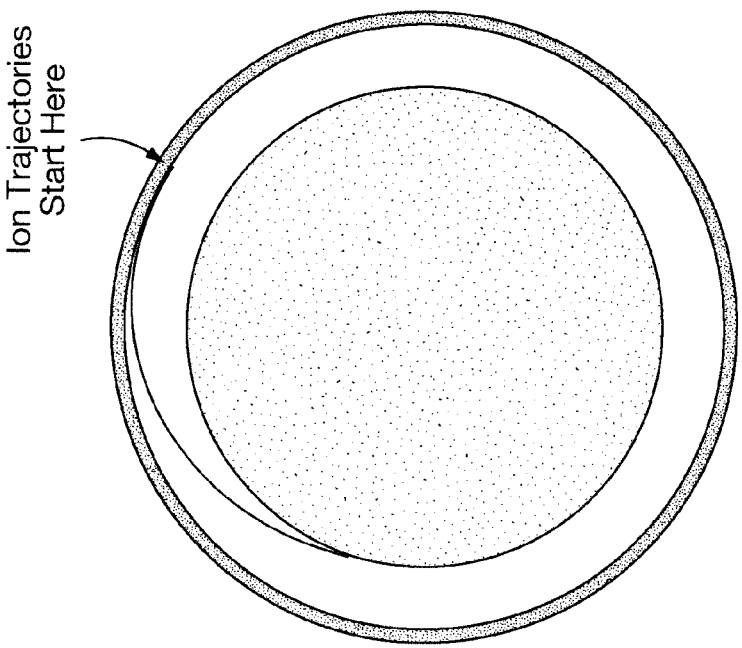
FIG. 22A shows the trajectory of an ion injected into an annular ion guiding region without scanning the internal field and FIG. 22B shows the trajectory of an ion injected into an annular ion guiding region with a higher energy and also without scanning the internal field.
Figure 22A:
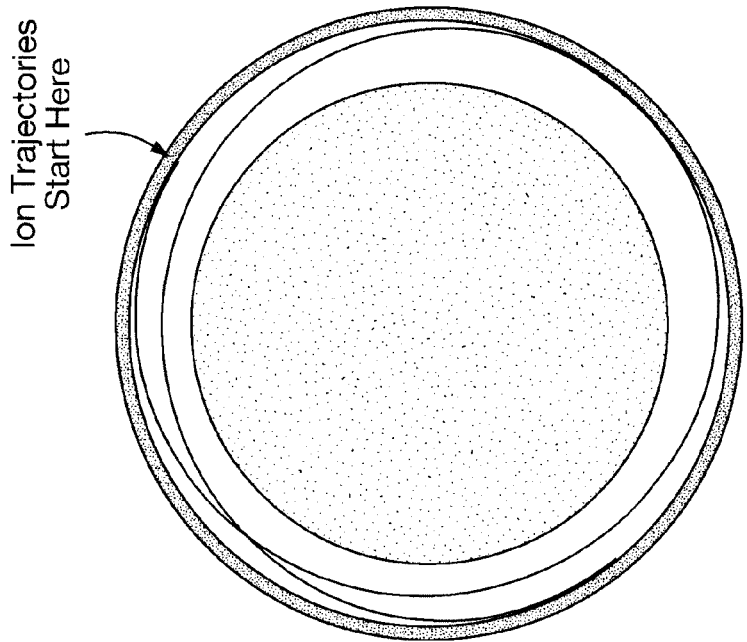

In FIG. 22A an ion is injected at an energy such that it would describe a circular trajectory halfway between the inner and outer cylinders if it were to find itself instantaneous created at such a position and with its velocity component entirely tangential to both cylinders. It can be seen that this ion is completely unstable quickly striking the inner cylinder after only about a quarter of one revolution.

In FIG. 22B the ion is injected at higher energy and is still unstable although it survives for about one and a half revolutions before it strikes the outer cylinder.

So it is desirable to find a way to inject ions into the instrument such that the fill factor is minimised and with little or no mass dependence on radial position within the device once the ions are in stable orbits.

The segmented coaxial cylinder geometry which is utilised according to the preferred embodiment enables different voltages to be applied to different segments and different portions of such segments as required. According to the preferred embodiment the acceleration region of the Time of Flight analyser is divided into two sectors. This allows control of the radial confining field with respect to sector angle and time. By pulsing the voltage to an angular portion of either the inner or outer cylinder the confining radial field may be pulsed ON or OFF.

FIG. 23A shows how in a preferred embodiment the device is split into two regions or sectors. With reference to the dials of a clock face the first region or sector (which extends from 12:00 o'clock around to 3:00 o'clock) is separated from the rest of the electrodes (which extend from 3:00 o'clock clockwise around to 12:00 o'clock).

FIG. 23A shows lines of equipotential and shows how ions that are injected at the top of the device from the right will experience a substantially field free flight in the first sector before they are deflected into the main radial sector in an anticlockwise direction. As the field is essentially static at this point mono energetic ions of differing mass take the same trajectory. This will be understood by those skilled in the art since this is a fundamental principle of electrostatics.

Whilst the ions are traversing around the main sector the small sector may be switched up to the same voltage as the main sector such that a continuous radial trapping field is created by the time the ions complete the circuit (see FIG. 23B). Such a scheme allows ion packets that are relatively long temporally to be injected into the device giving the Time of Flight mass analyser a high duty cycle of operation.

The preferred embodiment is therefore particularly advantageous in that it enables ions to be injected into the instrument such that the fill factor is minimised and with effectively zero mass dependence on radial position within the device once the ions are in stable orbits.

One of the problems with known multipass Time of Flight mass analysers is that it is difficult to determine the number of passes that a particular species of ion has traversed when detected. It is known to seek to address this problem by injecting a limited mass range into the mass analyser so that such aliasing is impossible. If a shorter temporal packet of ions is injected into the analyser then it may be possible to determine the mass by retaining the angular position of the ion packet when it strikes the detector.

With reference to FIGS. 24A-B three ions M1, M2, and M3 (where M1>M2>M3) may be injected into the mass analyser in a compact temporal packet. Immediately after injection in FIG. 24A it can be seen that the different masses have begun to separate rotationally. With a detector that retains angular information it is possible to predict the change in angle ϕ as each of the ions traverse the analyser. The combination of time of flight and angular position is enough to unequivocally determine the mass to charge (and therefore the number of roundtrips of the analyser) in certain cases. This extra angular information allows larger mass ranges to be injected into the analyser at any one time, so reducing the number of different spectra to be stitched together to cover the entire mass range.

Although the present invention has been described with reference to preferred embodiments, it will be understood by those skilled in the art that various changes in form and detail may be made without departing from the scope of the invention as set forth in the accompanying claims.

The invention claimed is:

1. A Time of Flight mass analyser comprising:
    an annular ion guide having a longitudinal axis and comprising a first annular ion guide section and a second annular ion guide section;
    a first device arranged and adapted to introduce ions into said first annular ion guide section, wherein an electric field is applied to the first annular guide section so that said ions form substantially stable circular orbits within said first annular ion guide section about said longitudinal axis;
    an ion detector disposed within said annular ion guide;
    a second device arranged and adapted to orthogonally accelerate ions in a first axial direction from said substantially stable circular orbits within said first annular ion guide section into said second annular ion guide section such that ions follow substantially spiral paths as they pass through said second annular ion guide section; and
    a third device arranged and adapted to maintain an axial DC potential along at least a portion of said second annular ion guide section so that, in use, said ions are reflected in a second axial direction which is substantially opposed to said first axial direction and so that said ions undergo multiple axial passes through said second annular ion guide section before being detected by said ion detector whereby the time of flight of the ions is measured.

2. A Time of Flight mass analyser as claimed in claim 1, wherein an ion detecting surface of said ion detector is positioned substantially at an isochronous plane.

3. A Time of Flight mass analyser as claimed in claim 1 wherein said second device is arranged and adapted to apply a pulsed axial electric field.

4. A Time of Flight mass analyser as claimed in claim 3, wherein said second device is further arranged and adapted to apply a pulsed radial electric field at substantially the same time as said pulsed axial electric field.

5. A Time of Flight mass analyser as claimed in claim 4, wherein said second device is arranged and adapted to apply a pulsed radial electric field at substantially the same time as said pulsed axial electric field so that said ions assume non-circular or elliptical orbits in a plane perpendicular to said longitudinal axis.

6. A Time of Flight mass analyser as claimed in claim 1, wherein said second device is arranged and adapted to orthogonally accelerate said ions into said second annular ion guide section so that said ions temporally separate according to their mass to charge ratio.

7. A Time of Flight mass analyser as claimed in claim 1, wherein said second device is arranged and adapted to orthogonally accelerate said ions so that time of flight dispersion occurs only in a longitudinal direction.

8. A Time of Flight mass analyser as claimed in claim 1, wherein said ion detector has an ion detecting surface which is arranged in a plane which is substantially perpendicular to said longitudinal axis.

9. A Time of Flight mass analyser as claimed in claim 1, wherein said ion detector has an annular, part annular or segmented annular ion detecting surface.

10. A Time of Flight mass analyser as claimed in claim 1, wherein said ion detector is located either: (i) substantially in the centre of said annular ion guide or said second annular ion guide section; (ii) substantially at an end of said annular ion guide or said second annular ion guide section; (iii) at an end of a field free region; (iv) adjacent said first annular ion guide section; or (v) distal to said first annular ion guide section.

11. A Time of Flight mass analyser as claimed in claim 1, wherein said annular ion guide comprises an inner cylindrical electrode arrangement.

12. A Time of Flight mass analyser as claimed in claim 11, wherein said inner cylindrical electrode arrangement is axially segmented and comprises a plurality of first electrodes.

13. A Time of Flight mass analyser as claimed in claim 12, wherein said annular ion guide comprises an outer cylindrical electrode arrangement.

14. A Time of Flight mass analyser as claimed in claim 13, wherein said outer cylindrical electrode arrangement is axially segmented and comprises a plurality of second electrodes.

15. A Time of Flight mass analyser as claimed in claim 14, wherein an annular time of flight ion guiding region is formed between said inner cylindrical electrode arrangement and said outer cylindrical electrode arrangement.

16. A Time of Flight mass analyser as claimed in claim 13, further comprising a device arranged and adapted to apply DC potentials to said inner cylindrical electrode arrangement and/or said outer cylindrical electrode arrangement in order to maintain a radial DC potential which acts to confine ions radially within said annular ion guide.

17. A Time of Flight mass analyser as claimed in claim 15, further comprising a control system arranged and adapted:
    (i) to apply one or more first voltages to one or more of said first electrodes and/or said second electrodes so that ions located in said first annular ion guide section precess or move in orbits about said inner cylindrical electrode arrangement; and then
    (ii) to apply one or more second voltages to one or more of said first electrodes and/or said second electrodes so that ions are orthogonally accelerated into said second annular ion guide section so that ions pass along spiral paths through said second annular ion guide section in a first axial direction;
    (iii) optionally to apply one or more third voltages to one or more of said first electrodes and/or said second electrodes so that ions are reflected back in a second axial direction which is opposed to said first axial direction; and
    (iv) to determine the time of flight of ions passing through said annular ion guide or said second annular ion guide section.

18. A Time of Flight mass analyser as claimed in claim 1, wherein said second device is arranged and adapted to apply a potential difference across said first annular ion guide section so that ions are orthogonally accelerated out of said first annular ion guide section and pass into said second annular ion guide section.

19. A Time of Flight mass analyser as claimed in claim 1, wherein said spiral paths are non-helical along at least a portion of said annular ion guide or said second annular ion guide section such that the ratio of curvature to torsion of said spiral paths varies or is non-constant.

20. A Time of Flight mass analyser as claimed in claim 1, further comprising a device arranged and adapted to maintain one or more half-parabolic or other DC potentials along a portion of said annular ion guide or said second annular ion guide section in order to reflect ions.

21. A Time of Flight mass analyser as claimed in claim 1, further comprising a device arranged and adapted to maintain one or more parabolic DC potentials along a portion of said annular ion guide or said second annular ion guide section so that ions undergo simple harmonic motion.

22. A Time of Flight mass analyser as claimed in claim 1, wherein said annular ion guide or said second annular ion guide section comprises one or more reflectrons for reflecting ions in a reverse axial direction.

23. A Time of Flight mass analyser as claimed in claim 1, wherein said second device is arranged to orthogonally accelerate ions at a time $T_1$ and wherein said ions are detected by said ion detector at a subsequent time $T_2$ and wherein ions having a mass to charge ratio in the range <100, 100-200, 200-300, 300-400, 400-500, 500-600, 600-700, 700-800, 800-900 or 900-1000 are arranged to have a total time of flight $T_2-T_1$ through said annular ion guide or said second annular ion guide section selected from the group consisting of: (i) <50 µs; (ii) 50-100 µs; (iii) 100-150 µs; (iv) 150-200 µs; (v) 200-250 µs; (vi) 250-300 µs; (vii) 300-350 µs; (viii) 350-400 µs; (ix) 400-450 µs; (x) 450-500 µs; and (xi) >500 µs.

24. A Time of Flight mass analyser as claimed in claim 1, wherein ions having different mass to charge ratios follow substantially different spiral paths through said annular ion guide or said second annular ion guide section.

25. A Time of Flight mass analyser as claimed in claim 1, wherein electrodes in said first annular ion guide section are segmented so that at least a first electric field sector and a second electric field sector are formed in use.

26. A Time of Flight mass analyser as claimed in claim 25, further comprising a control system arranged and adapted at a first time T1 to inject ions substantially tangentially into said first electric field sector whilst maintaining a substantially zero radial electric field in said first electric field sector so that said ions experience a substantially field free region whilst being injected into said first annular ion guide section.

27. A Time of Flight mass analyser as claimed in claim 26, wherein said control system is further arranged and adapted to maintain a radial electric field in said second electric field sector so that at a second later time T2 ions pass from said first electric field sector into said second electric field sector and become radially confined.

28. A Time of Flight mass analyser as claimed in claim 27, wherein said control system is further arranged and adapted at a third time T3, wherein T3>T1, to cause a radial electric field to be maintained in said first electric field sector so that as ions pass from said second electric field sector into said first electric field sector said ions continue to be radially confined and form substantially stable circular orbits within said first annular ion guide section.

29. A Time of Flight mass analyser as claimed in claim 28, wherein said second device is arranged and adapted to orthogonally accelerate ions from said first annular ion guide section into said second annular ion guide section at a fourth time T4, wherein T4>T3.

30. A Time of Flight mass analyser as claimed in claim 1, further comprising a control system arranged and adapted to determine the time of flight of said ions orthogonally accelerated from said first annular ion guide section into said second annular ion guide section.

31. A Time of Flight mass analyser as claimed in claim 1, wherein said ion detector is arranged and adapted to detect ions impacting or impinging upon an ion detection surface of said ion detector.

32. A mass spectrometer comprising a Time of Flight mass analyser as claimed in claim 1.

33. A method of mass analysing ions comprising:
providing an annular ion guide having a longitudinal axis and comprising a first annular ion guide section and a second annular ion guide section;
introducing ions into said first annular ion guide section;
applying an electric field to said first annular ion guide section so that said ions form substantially stable circular orbits within said first annular ion guide section about said longitudinal axis;
providing an ion detector disposed within said annular ion guide;
orthogonally accelerating ions in a first axial direction from said substantially stable circular orbits within said first annular ion guide section into said second annular ion guide section such that ions follow substantially spiral paths as they pass through said second annular ion guide section; and
maintaining an axial DC potential along at least a portion of said second annular ion guide section so that said ions are reflected in a second axial direction which is substantially opposed to said first axial direction and so that said ions undergo multiple axial passes through said second annular ion guide section before being detected by said ion detector.

34. A method of mass spectrometry comprising a method of mass analysing ions as claimed in claim 33.

35. A method of mass analysing ions as claimed in claim 33 whereby the time of flight of the ions is measured.

* * * * *